(12) United States Patent
Pugh et al.

(10) Patent No.: US 11,981,777 B2
(45) Date of Patent: May 14, 2024

(54) SYNTHESIS OF HYPERBRANCHED POLYMETHACRYLATES AND POLYACRYLATES BY A HALOINIMER APPROACH

(71) Applicants: Coleen Pugh, Akron, OH (US); Chenwei Liu, Patchogue, NY (US); Cesar Lopez Gonzalez, Akron, OH (US); Chenying Zhao, Houston, TX (US)

(72) Inventors: Coleen Pugh, Akron, OH (US); Chenwei Liu, Patchogue, NY (US); Cesar Lopez Gonzalez, Akron, OH (US); Chenying Zhao, Houston, TX (US)

(73) Assignee: The University of Akron, Akron, OH (US)

( * ) Notice: Subject to any disclaimer, the term of this patent is extended or adjusted under 35 U.S.C. 154(b) by 1087 days.

(21) Appl. No.: 16/545,470

(22) Filed: Aug. 20, 2019

(65) Prior Publication Data

US 2020/0055995 A1 Feb. 20, 2020

Related U.S. Application Data

(60) Provisional application No. 62/719,880, filed on Aug. 20, 2018.

(51) Int. Cl.
| | | |
|---|---|---|
| *C08G 83/00* | (2006.01) | |
| *A61L 15/24* | (2006.01) | |
| *A61L 15/64* | (2006.01) | |
| *A61L 26/00* | (2006.01) | |
| *C07K 1/14* | (2006.01) | |
| *C08F 20/68* | (2006.01) | |
| *C09D 135/02* | (2006.01) | |

(52) U.S. Cl.
CPC ............ *C08G 83/005* (2013.01); *A61L 15/24* (2013.01); *A61L 15/64* (2013.01); *A61L 26/0014* (2013.01); *A61L 26/009* (2013.01); *C07K 1/145* (2013.01); *C08F 20/68* (2013.01); *C09D 135/02* (2013.01)

(58) Field of Classification Search
CPC ........ C08G 83/005; C08F 20/68; C08F 20/22; C08F 2438/01; C09D 135/02; C09D 133/16; A61L 15/24; A61L 27/34; A61L 26/0014
USPC ......................................................... 526/75
See application file for complete search history.

(56) References Cited

U.S. PATENT DOCUMENTS

| | | |
|---|---|---|
| 4,025,450 A | 5/1977 | Lamberti et al. |
| 5,155,043 A | 10/1992 | Murakami et al. |
| 6,100,350 A | 8/2000 | Wilczek et al. |
| 6,107,408 A | 8/2000 | Quirk et al. |
| 6,156,859 A | 12/2000 | Langstein et al. |
| 6,177,562 B1 | 1/2001 | Uggeri et al. |
| 6,812,298 B2 | 11/2004 | Dvornic et al. |
| 8,524,942 B2 | 9/2013 | Pugh et al. |
| 2011/0046334 A1 | 2/2011 | Pugh et al. |

FOREIGN PATENT DOCUMENTS

| | | | |
|---|---|---|---|
| EP | 1 688440 A1 | 8/2006 | |
| WO | 2008045299 A1 | 4/2008 | |
| WO | WO 2008/045299 A1 * | 4/2008 | ................ C12P 7/02 |

OTHER PUBLICATIONS

Garcia et al., Polymer Preprints, American Chemical Society, Division of Polymer Chemistry, 2011, 52(1).*
Dabritz et al., Polymer, 2011, 52, 5723-5731.*
Paulssen et al, The Journal of Organic Chemistry, 1969, 34(7), 2097-2101.*
Sherk et al, Journal of the American Chemical Society, 1945, 67(12), 2239-2240.*
Hubbard et al, J. Org. Chem. 1998, 63, 677-683.*
But et al, Chem. Asian J., 2007, 2, 1340-1355.*
Shelkov et al, Org. Biomol. Chem., 2004, 2, 397-401.*
Yadav et al, Reactive and Functional Polymers, 2002, 52, 99-110.*
Karen L. Wooley. et al., "Influence of shape on the reactivity and properties of dentritic, hyperbranched and linear aromatic polyesters", Polymer, vol. 35, No. 21, 1994, pp. 4489-4495.
Gao, C., et ai, "Hyperbranched Polymers: From Synthesis to Applications," Prog. Polym. Sci., 29, 183-275 (2004).
Busson, P., et al., "Preparation of Mesogen-Functionalized Dendrimers for Second-Order Nonlinear Optics," Macromolecules, 35, 1663-1671 (2002).
Sunder, M.F. Quicny, et al., "Hyperbranched Polyether Polyols with Liquid Crystalline properties," Angew. Chem. In!. Ed., 38, 2928-2930 (1999).
Peng, H., et al., "Simple Synthesis, Outstanding Thermal Stability and Optical-Limiting Properties of Functional Hyperbranched Polyarylenes," Macromolecules, 35, 5349-5351 (2002).
Percec, V., "Molecular Design of Novel Liquid Crystalline Polymers with Complex Architecture: Macrocyclics and Dendrimers", Pure Appl. Chem., 67, 2031-2038 (1995).
Kricheldorf, H.R., et al., "New Polymer Syntheses. XCVII. Hyperbranched LC-Polyesters Based on 6-(4-Hydroxyphenyl)propionic Acid and 4-Hydroxybenzoic Acid", J. Polym. Sci., Polym. Chem. Ed., 36, 1397-1405 (1998).
Hawker, C.J., et al., "Preparation of Hyperbranched and Star Polymers by a 'Living,' Self-Condensing Free Radical polymerization," J. Am. Chem. Soc., 117, 10763-10764 (1995).

(Continued)

*Primary Examiner* — Ganapathy Krishnan

(74) *Attorney, Agent, or Firm* — Renner, Kenner, Greive, Bobak, Taylor & Weber

(57) ABSTRACT

A new synthetic pathway for hyperbranched polyacrylates and polymethacrylates including the steps of preparing an inimer and polymerizing the inimer to form hyperbranched polymers or copolymers.

9 Claims, 4 Drawing Sheets

(4 of 4 Drawing Sheet(s) Filed in Color)

(56) References Cited

OTHER PUBLICATIONS

Frechet, J.M.J., et al., "Self-Condensing Vinyl Polymerization: An Approach to Dendritic Materials," Science, 269, 1080-1083 (1995).
Gaynor, et al., "Synthesis of Branched and Hyperbranched Polystyrenes," Macromolecules, 29,1079-1081 (1996).
Weimer, M.W., et al., "Importance of Active-Site Reactivity and Reaction Conditions in the Preparation of Hyperbranced Polymers by Self-Condensing Vinyl Polymerization: Highly Branched vs. Linear Poly[4-(chloromethyl) styrene] by Metal-Catalyzed 'Living' Radical polymerization," J. Polym. Sci., Polym. Chem. Ed., 36, 955-970 (1998).
Shizu, K., et al., "Kinetics of Hyperbranched Polystyrenes by Free Radical polymerization of Photofunctionallnimer", Macromolecules, 35, 3781-3784 (2002).
Matyjaszewski, K., et al., Preparation of Hyperbranched Polyacrylates by Atom Transfer Radical Polymerization. 1. Acrylic Ab* Monomers in "Living" Radical Polymerizations, Macromolecules, 30, pp. 5192-5194; 2. Kinetics and Mechanism of Chain Growth for the Self-Condensing Vinyl Polymerization of 2-«2-Bromopropionyl)oxy)ethyl Acrylate, pp. 7034-7041; and 3. Effect of Reaction Conditions on the Self-Condensing Vinyl Polymerization pf2-«2-, 1997.
Yoo, S.H., et al., "Synthesis of Hyperbranched Polyacrylates in Emulsion by Atom Transfer Radical polymerization," Macromolecules, 35, 1146-1148 (2002).
Shizu, K., et al., "Synthesis and Characterization of Hyperbranched Poly(ethyl methacrylate) by Quasi-Living Radical Polymerization of a Photofunctionallnimer", Polym. Int., 51, 424-428 (2002).
Lovell, PA, et al., "Chain Transfer to Polymer in Emulsion Polymerization of n-Butyl Acrylate Studied by 13C NMR Spectroscopy and Gel Permeation Chromatography", Polymer Commun., 32,98-103 (1991).
Ahmad, N.M., et al., "Chain Transfer to Polymer in Emulsion Polymerization", Macromol. Symp., 143,231-241 (1999).
Heatley, F., et al., "Chain Transfer to Polymer in Free-Radical Solution Polymerization of 2-Ethylhexyl Acrylate Studied by NMR Spectroscopy", Macromolecules, 34 7636-7641 (2001).
Britton, D.J., et al., Macromol. Symp 175,95-104 (2001).
Farook, S.A.M., et al., "Kinetics and Mechanism of Bromine Addition to Derivatives of Unsaturated Aliphatic Carboxylic Acids in Aqueous Solution", Bull. Chem. Soc, Jpn., 57, 1394-1400 (1984).
Mattocks, AM., et al., "A Synthesis of Serine and Its Methyl Ester", J. Biol. Chem., 165,501-503 (1946).
Bell, R.P., et al., "Kinetics of the Reactions of Olefins and Halogens in Aqueous Solution. Part III. Reaction of Bromine with Acrylic Acid, Crotonic Acid and Ethyl Acrylate", J. Chem. Soc. (B), 500-503 (1968).
Slieker, L., et al., A Convenient Synthesis of 2S, 3S-Serine-3-D and 2S,3R-Serine-2,3-D2, J. Labelled Compd. Radiopharmaceuticals, 19,647-657 (1982).
Leibman, K.C., et al., "Synthesis and Properties of Isoserine. A Novel Bromohydrination Method", J. Org. Chem., 27, 438-440 (1962).
Archeveque, M., et al., "A Simple Preparation of R or S Glycidic Esters; Application to the Synthesis of Enantiomerically Pure a-Hydroxyesters," Tetrahedron Lett., 28, 1993-1996 (1987).
Shimohigashi, Y., et al., "Walden Inversion of Amino Acids. VIII. Stereospecific Synthesis of D-Isoserine and D-Isothreonine from L-Serine and L-Threonine, Memoirs Faculty Sci., Kyushu Univ., 11,217-224 (1978).
Muller, AH.E., et al., "Molecular Parameters of Hyperbranched Polymers Made by Self-Condensing Vinyl Polymerization. 1. Molecular Weight Distribution," Macromolecules, 30, 7015-7023 (1997).
Yan, D., et al., "Molecular Parameters of Hyperbranched Polymers Made by Self-Condensing Vinyl Polymerization. 2. Degree of Branching," Macromolecules, 30, 7024-7033 (1997).
Litvinenko, G.I., et al., "Molecular Parameters of Hyperbranched Copolymers Obtained by Self-Condensing Vinyl Copolymerization. 1. Equal Rate Constants," Macromolecules, 32, 2410-2419 (1999).
Schon, F., et al., "New Strategy for the Synthesis of Halogen-Free Acrylate Macromonomers by Atom Transfer Radical Polymerization," Macromolecules, 34, 5394-5397 (2001).
Mori, et al., Surface-Grafted Hyperbranched Polymers by Self-Condensing Vinyl (co)Polymerization Via ATRP. Lehrstuhl fur Makromolekular Chemie II and Bayreuther Zentrum fur Kollorde und Grenzflachen Universitat Bayreuth, 2003, p. 1-2.
Belikov, V.M. Vllt, S.V. Kuznelsova, N.I., Bezrukov, M.G., & Saporovskaya, M.B. (1965) Reaction of the copper complex of L-alanine with actaldehyde and the mechanism of the akabori reaction, Russian Chemical 18(11), 2371-2375. http://doi.org/10.1007/BF00906512.
Belikov, V.M. Kuznetsova, N.I. & Safonova, E.N. (1967). Study of the condition of obtaining the copper complex of threonine. Chemistry of Natural . . . ,3(1), 25-28. http://doi.org/10.1007/bf01171717.
Zheng, Y. Li, S., Weng, Z., & Gao, C. (2015). Hyperbranched polymers: advances from synthesis to applications. Chemical Society Reviews, 44(12), 4091-4130. http://doi.org/10.1039/c4cs00528g.
Otani, T.T,; Winitz, M. Archives of Biochemistry and Biophysics 1960, 90, 254-259.
Pugh, C.; Singh, A.; Samuel, R.; Bernal Ramos, K.M. Macromolecules 2010, 43, 5222-5232.
Pugh, C.; Raveendra, B.; Singh, A.; Samuel, R.; Garcia, G. Synlett 2010, 1947-1950.
Lu, Y.; Debnath, D.; Weiss, R.; Pugh, C.J. Polym. Sci. Part A Polym. Chem. 2015, 53, 2399-2410.
Lin, K.; Kasko, A.M. Biomacromolecules 2013, 14, 350-357.
Lin, K.; Kasko, A.M. Bioconjug. Chem. 2015, 1504-1512.
Wang, J.S.; Matyjaszewski, K. Controlled/ "Living" Radical Polymerization. Atom Transfer Radical Polymerization in the Presence of Transition-Metal Complexes. J. Am. Chem. Soc. 1995, 117, 5614-5615.
Ando, T.; Kamigaito, M.; Sawamoto, M. Iron(II) Chloride Complex for Living Radical Polymerization of Methyl Methacrylate. Marcomolecules 1997, 30, 4507-4510.

\* cited by examiner

| Entry | Polymer Architecture | Time h | [Inimer]:[Monomer]:[I]:[CuBr]:[PMDETA]:[R.A.] | Conversion % | Yield % | $M_n$ (kDa) GPC | $Đ$ (PDI) GPC | $M_n$ (kDa) LS | $Đ$ (PDI) LS | $\bar{X}_n$ |
|---|---|---|---|---|---|---|---|---|---|---|
| 1[f] | Linear | 96 | 0:24:1:1:1:0[b] | 79 | 70 | 4.50 | 1.28 | 9.80 | 1.21 | 24 |
| 2[f] | SN&RI | 96 | 0:40:1:1:1:0[b] | 77 | 50 | 8.00 | 1.57 | 21.5 | 1.31 | 53 |
| 3[f] | | 96 | 0:50:1:1:1:0[b] | 73 | 57 | 10.1 | 1.48 | 27.5 | 1.25 | 68 |
| 4[f] | | 96 | 0:100:1:1:1:0[b] | 71 | 52 | 20.8 | 2.03 | 52.1 | 1.55 | 130 |
| 5[f] | Hyperbranched SN&RI | 48 | 10:0:0.25:1:1:0[b] | 61 | 51 | 6.00 | 1.52 | 47.1 | 1.23 | 83 |
| 6[f] | | 60 | 10:0:0.25:1:1:0[b] | 68 | 60 | 8.10 | 1.60 | 57.1 | 1.37 | 100 |
| 7[f] | | 72 | 10:0:0.25:1:1:0[b] | 74 | 66 | 12.7 | 2.08 | 113 | 1.43 | 199 |
| 8[f] | | 84 | 10:0:0.25:1:1:0[b] | 79 | 73 | 14.6 | 2.22 | 130 | 1.29 | 229 |
| 9[f] | | 96 | 10:0:0.25:1:1:0[b] | 84 | 77 | 18.1 | 2.10 | 182 | 1.36 | 320 |
| 10 | Hyperbranched ARGET | 24 | 10:0:0:1:1:5[c] | 82 | 52 | 0.500 | 1.04 | 0.800 | 1.36 | 1 |
| 11 | | 36 | 10:0:0:1:1:5[c] | 84 | 53 | 1.10 | 1.01 | 38.6 | 1.38 | 68 |
| 12 | | 122 | 10:0:0:1:1:5[c] | 81 | 56 | 1.60 | 1.60 | 98.7 | 1.37 | 173 |
| 13 | | 213 | 10:0:0:1:1:5[c] | 89 | 58 | 4.00 | 1.56 | 171 | 1.31 | 300 |
| 14 | Hyperbranched SN&RI | 3.7 | 50:0:0.62:1:1:0[d] | >92 | 65 | 5.28 | 1.79 | 15.3 | 1.33 | 30 |
| 15 | | 4.7 | 50:0:0.62:1:1:0[d] | >92 | 65 | 5.60 | 1.79 | 16.4 | 1.38 | 32 |
| 16 | | 8.0 | 50:0:0.62:1:1:0[d] | >92 | 65 | 7.69 | 1.94 | 38.0 | 1.21 | 75 |
| 17 | | 8.5[a] | 50:0:0.62:1:1:0[d] | >94 | 0.2 | -- | -- | -- | -- | -- |

| Lectin/carbohydrate solution | Δf Hz | Δm ng/cm² | Moles/cm² *10¹² | Monosaccharide units *10¹² | Polymer/Lectin mole ratio | Galactose/lectin mole ratio |
|---|---|---|---|---|---|---|
| Con A | 44.7 | 108.5 | 1.02 | 0 | 1 | - |
| Con A desorption (Galactose Sn) | -3.5 | -8.5 | -8.02*10⁻² | 0 | - | - |
| RCA120 | 60.9 | 151.9 | 1.28 | 0 | 1 | 1 |
| HB Polymer (61.5 kDa) | 15.2 | 38.5 | 6.26*10⁻¹ | 9.14 | 0.49 | 71.4 |
| RCA120 | 59.3 | 144.6 | 1.19 | 0 | 1 | 1 |
| Linear Polymer (39.6 kDa) | 2.5 | 6.1 | 1.54*10⁻¹ | 1.94 | 0.13 | 16.3 |
| PNA | 30.0 | 72.9 | 6.62*10⁻¹ | 0 | 1 | 1 |
| HB Polymer (61.5 kDa) | 8.8 | 21.2 | 3.45*10⁻¹ | 5.04 | 0.52 | 76.2 |
| PNA | 40.0 | 97.1 | 8.83*10⁻¹ | 0 | 1 | 1 |
| Linear Polymer (39.6 kDa) | 2.1 | 0.9 | 2.02*10⁻² | 2.7*10⁻¹ | 0.02 | 2.88 |

Figure 4

SYNTHESIS OF HYPERBRANCHED POLYMETHACRYLATES AND POLYACRYLATES BY A HALOINIMER APPROACH

CROSS-REFERENCE TO RELATED APPLICATIONS

This application claims the benefit of U.S. Provisional Patent Application No. 62/719,880, filed Aug. 20, 2018, which is incorporated herein by reference.

STATEMENT REGARDING FEDERALLY SPONSORED RESEARCH OF DEVELOPMENT

This invention was made with government support under award number CHE-1112326 awarded by the National Science Foundation. The government has certain rights in the invention.

FIELD OF THE INVENTION

The present invention generally resides in the field of methods to prepare hyperbranched polyacrylates and polymethacrylates.

BACKGROUND OF THE INVENTION

As a vital class of dendritic polymers, hyperbranched polymers are interesting to both academia and industry for their three-dimensional highly-branched architecture, abundant functional groups, and unique properties. Hyperbranched polymers exhibit a special polymer architecture that strongly influences polymer properties, degradability and functionality compared to linear analogs, including low viscosity, high solubility in many solvents. The multiple end groups are available for additional functionalization and to introduce high functionality for desired applications. Furthermore, our hyperbranched glycopolymers offer special biological properties that cannot be found in commodity linear polymers. Furthermore, hyperbranched glycopolymers contain carbohydrates as a substituent from the polymer backbone and are useful for biomedical applications such as protein preservation.

Self-condensing vinyl polymerization (SCVP) provides an efficient approach for synthesis of hyperbranched polymers. WO 2008/045299 A1, incorporated herein by reference, describes inimers and processes for making them. The inimers may be polymerized to form hyperbranched polymers. The synthesis of inimers and hyperbranched polymers are also discussed in Pugh, C.; Singh, A.; Samuel, R.; Bernal Ramos, K. M., "Synthesis of Hyperbranched Polyacrylates by a Chloroinimer Approach", Macromolecules 2010, 43, 5222-5232, and Pugh, C.; Raveendra, B.; Singh, A.; Samuel, R.; Garcia, G., "Design and Regioselective Synthesis of (2-Bromo-2-akloxycarbonyl)ethyl Acrylates as Inimers for Hyperbranched (Co)Polyacrylates", SynLett 2010, 13, 1947-1950.

However, additional chemical processes for preparing a wide variety of hyperbranched polyacrylates and polymethacrylates with reduced side reactions are desirable.

SUMMARY OF THE INVENTION

Advantageously, the present invention is based upon the discovery of convenient and effective methods to synthesize hyperbranched polyacrylates and polymethacrylates through self-condensing vinyl polymerization (SCVP) and copolymerization with monomers through self-condensing vinyl copolymerization (SCVCP). The resulting hyperbranched polymethacrylates are architecturally analogous to linear polymethacrylates.

In one or more embodiments of the invention, inimers having a free alkyl ester substituent, in addition to a methacrylate or acrylate and alpha-halofunctional groups, can be homopolymerized to produce hyperbranched polymethacrylates having a wide variety of substituents. The hyperbranched polymethacrylates prepared by the method of the present invention are characterized by a very high degree of branching.

One or more embodiments of the present invention provides A method for preparing hyperbranched polyacrylates or polymethacrylates, the method comprising (a) reacting a halohydrin containing a carboxylic acid group with an anhydride in the presence of an acid catalyst, to form a pre-inimer that contains a carboxylic acid group; (b) reacting the pre-inimer with a chlorinating agent to form an acid chloride; (c) reacting the acid chloride with an alcohol in the presence of trimethylamine to esterify the acid chloride and form an inimer; and (d) polymerizing the inimer to form a hyperbranched polyacrylate or polymethacrylate polymer by self-condensing vinyl polymerization, or copolymerizing the inimer with one or more monomers using self-condensing vinyl co-polymerization.

One or more embodiments of the present invention provides a method for preparing hyperbranched polyacrylates or polymethacrylates, the method comprising (a) reacting a halohydrin containing a carboxylic acid group with an anhydride in the presence of an acid catalyst, to form a pre-inimer that contains a carboxylic acid group; (b) reacting the pre-inimer with an alcohol using carbodiimide coupling or a Mitsunobu reaction to form an ester inimer; and (c) polymerizing the inimer to form a hyperbranched polyacrylate or polymethacrylate polymer by self-condensing vinyl polymerization, or copolymerizing the inimer with one or more monomers using self-condensing vinyl co-polymerization.

One or more embodiments of the present invention provides a hyperbranched polyacrylate or polymethacrylate polymer or copolymer prepared according to the methods of the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is a tabular summary of Linear and hyperbranched polymerization from monomers brominated inimers and chlorinated inimer analogs using SN&RI and ARGET ATRP. Entry 1-13: Polymerizations in anisole [M]=1.56 M at 110 o C. Entry 14-17: Polymerizations in toluene [M]=9.8 mM at 80 oC a) [Initiator]=2-bromo-3-acetyl-methyl propionate, [Monomer]=α,β-1,2,3,4-tetra acetyl-6-O-acryloyl mannopyranose b) [Initiator]=AIBN [Inimer]=α,β-[3-acrylate-2-bromo-6-O-α,β-(1,2,3,4-O-tetraacetyl) mannopyranose propionate][Inimer]:[0]:[AIBN]:[CuBr2]:[PMDETA] c) [Inimer]:[0]:[CuBr2]:[PMDETA]:[Cu(0)] d) [InimerCl]=3-acrylate-2-chloro-6-O-α,β-(1,2,3,4-O-tetraacetyl)mannopyranose propionate (37b,38b) [InimerCl]:[0]:[AIBN]:[CuCl2]:[Wang-Pugh's ligand]:[0] at 80o C. e) Insoluble gel.

Figure 2:
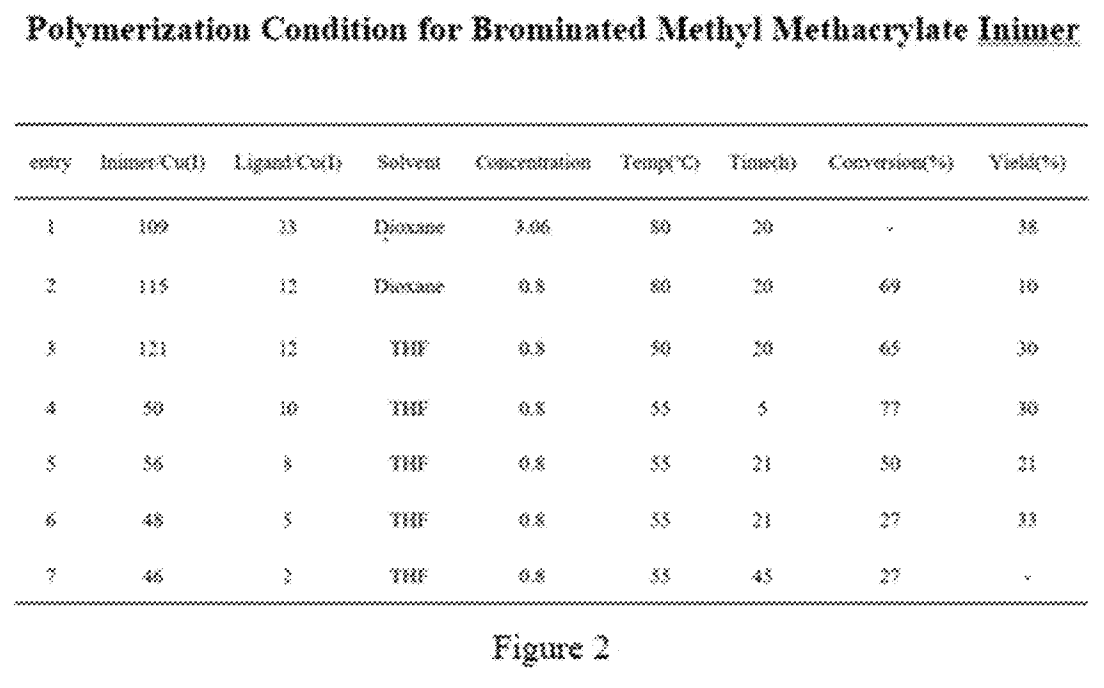

FIG. 2 is a tabular summary of Polymerization Condition for Brominated Methyl Methacrylate Inimer.

FIG. 4 is a tabular summary of Polymer/lectin adsorption results based on the frequency reported by the quartz crystal microbalance.

DETAILED DESCRIPTION OF ILLUSTRATIVE EMBODIMENTS

Figure 3:
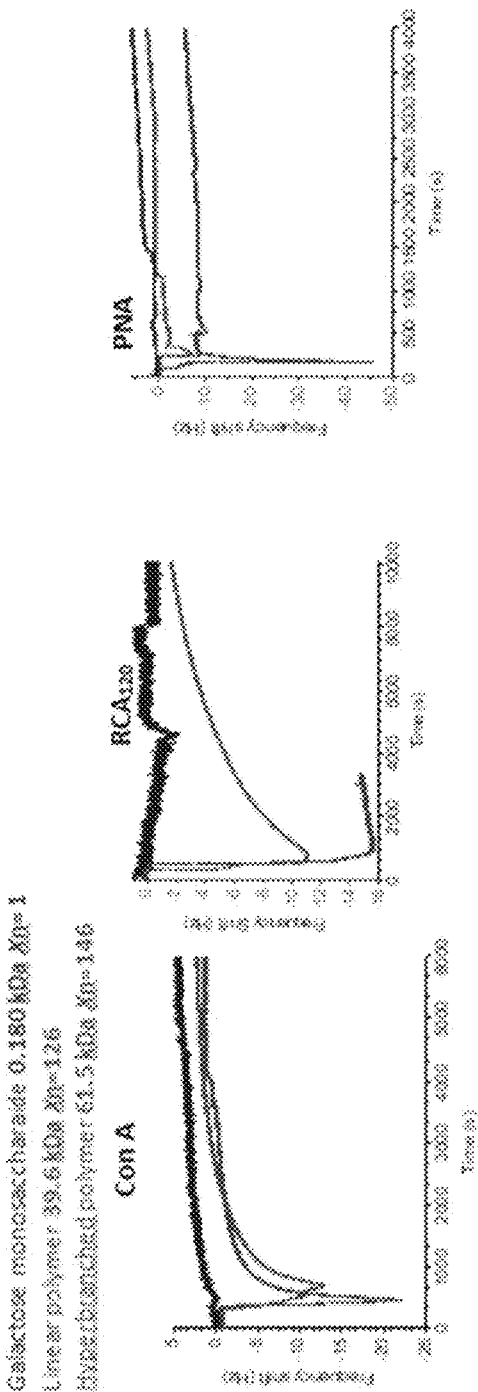
FIG. 3 illustrates Quartz crystal microbalance adsorption test D-Galactose solution, linear and hyperbranched glycopolymers with lectins with Con A, RCA$_{120}$ and PNA at a flow rate of 1.5 mL/min. Galactose monosaccharaide 0.180 kDa Xn=1 shown in blue; Linear polymer 39.6 kDa Xn=126 shown in red; and Hyperbranched polymer 61.5 kDa Xn=146 shown in purple.

The present invention provides a new synthetic pathway for hyperbranched polyacrylates and polymethacrylates. Very generally, the method of the present invention includes the steps of preparing an inimer and polymerizing the inimer to form a polymer, or copolymerizing the inimer with one or more monomers to form a copolymer.

In one or more embodiments, a method is provided for preparing hyperbranched polymethacrylates, the method including the steps of: (a) reacting a halohydrin containing a carboxylic acid group with an anhydride in the presence of an acid catalyst, to form a pre-inimer that contains a carboxylic acid group; (b) reacting the pre-inimer with a chlorinating agent to form an acid chloride; (c) reacting the acid chloride with an alcohol in the presence of trimethylamine to esterify the acid chloride and form an inimer; and (d) polymerizing the inimer to form a hyperbranched polymethacrylate polymer by self-condensing vinyl polymerization, or copolymerizing the inimer with one or more monomers using self-condensing vinyl co-polymerization.

In one or more embodiments, a method is provided for preparing hyperbranched polymethacrylates, the method including the steps of: (a) reacting a halohydrin containing a carboxylic acid group with an anhydride in the presence of an acid catalyst, to form a pre-inimer that contains a carboxylic acid group; (b) reacting the pre-inimer with an alcohol using carbodiimide coupling or a Mitsunobu reaction to form an ester inimer; and (d) polymerizing the inimer to form a hyperbranched polymethacrylate polymer by self-condensing vinyl polymerization, or copolymerizing the inimer with one or more monomers using self-condensing vinyl co-polymerization.

Preparation of D,L-Methyl Serine

A reactant that may be employed in the synthetic pathway is D,L-methyl serine. Advantageously, D,L-methyl serine may be synthesized by way of an Akabori reaction in an alkaline aqueous solution of alanine with an excess of formaldehyde in the presence of catalytic amounts of cupric ion (Scheme 1).

Scheme 1. Synthesis of D, L-methyl serine from D,L-alanine.

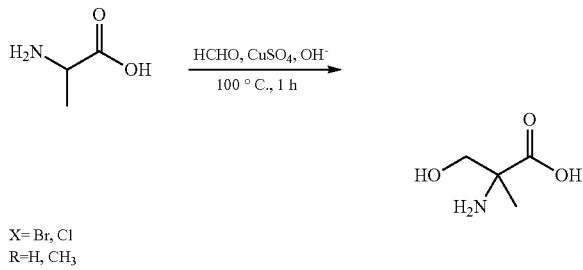

X= Br, Cl
R=H, CH$_3$

Preparation of a Halohydrin Containing a Carboxylic Acid

A halohydrin containing a carboxylic acid group may be synthesized by deaminohalogenation of D,L-methyl serine. For example, the halohydrin 2-bromo-2-methyl-3-hydroxyl propionic acid may be synthesized by deaminphalogenation of D,L-methyl serine, as shown in Scheme 2A, where X is selected from Br and Cl, and where R is selected from hydrogen and methyl.

Scheme 2A. Deaminohalogenation of methyl serine

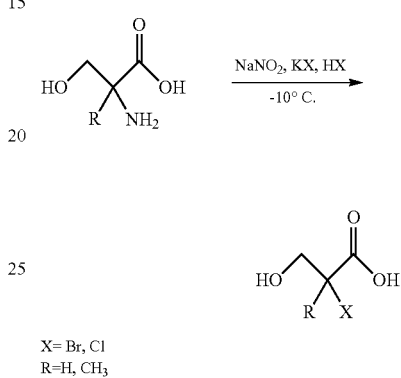

X= Br, Cl
R=H, CH$_3$

Scheme 2B. Direct oxidation of halogenated propanediol to synthesize 2-halo-3-hydroxy-propionic acid or 2-halo-2-methyl-3-hydroxy-propionic acid

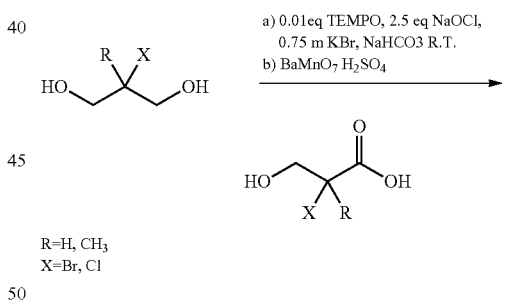

R=H, CH$_3$
X=Br, Cl

In other embodiments, a halohydrin containing a carboxylic acid group may be prepared by reacting one of the following reaction Schemes 2B or 2C: Scheme 2B represents the direct oxidation of a halogenated diol such as 2-(halo)-2-methylpropane-1,3-diol to obtain 2-bromo-2-methyl-3-hydroxylpropionic acid using an oxidizing agent such as 2,2,6,6-Tetramethylpiperidinyloxy TEMPO and sodium hypochlorite.

Scheme 2C represents the selective protection of a single alcohol of the halogenated propanediol or butanediol using silyl ethers such as trimethyl silyl ether to obtain the intermediate alcohol-free reagent. The intermediate alcohol may be subsequently oxidized to a carboxylic acid using an oxidizing agent. Finally, the deprotection of the silyl ether protecting group may be performed under acidic conditions.

Scheme 2C. Selective alcohol protection and oxidation to synthesize 2-halo-3-hydroxy-propionic acid or 2-halo-2-methyl-3-hydroxypropionic acid

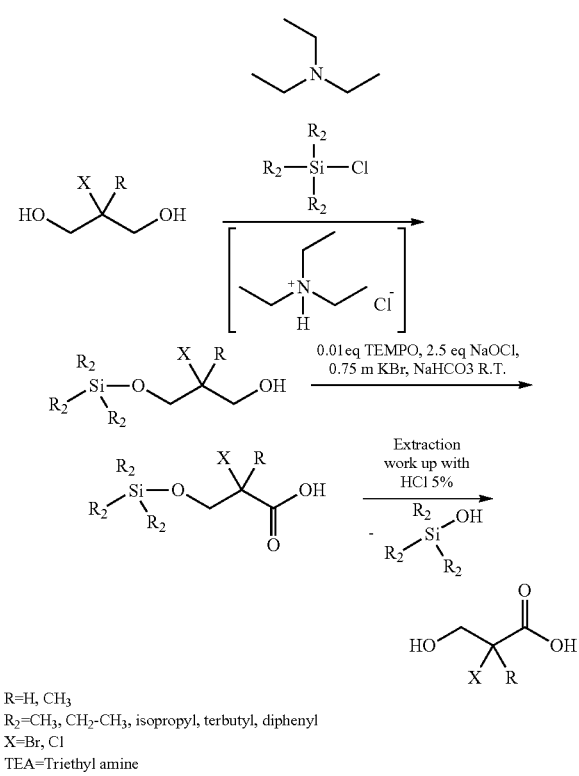

R=H, CH₃
R₂=CH₃, CH₂-CH₃, isopropyl, terbutyl, diphenyl
X=Br, Cl
TEA=Triethyl amine Preparation of Pre-Inimer Acid In one or more embodiments, a halohydrin containing a carboxylic acid group may be reacted with an acrylic or methacrylic anhydride through acid-catalyzed esterification to form a pre-inimer as shown in Scheme 3. Acrylolyl chloride or methacryloyl chloride may be used instead of the anhydride under appropriate conditions. The pre-inimer contains a carboxylic acid group and a polymerizable acrylate or methacrylate group. For example, 2-bromo-2-methyl-3-hydroxypropionic acid may be reacted with methacrylic anhydride in the presence of an acid catalyst such as p-toluenesulfonic acid (p-TOH), to synthesize 3-methacrylate-2-bromo-2-methylpropionic acid.

Scheme 3. Synthesis of pre-inimer

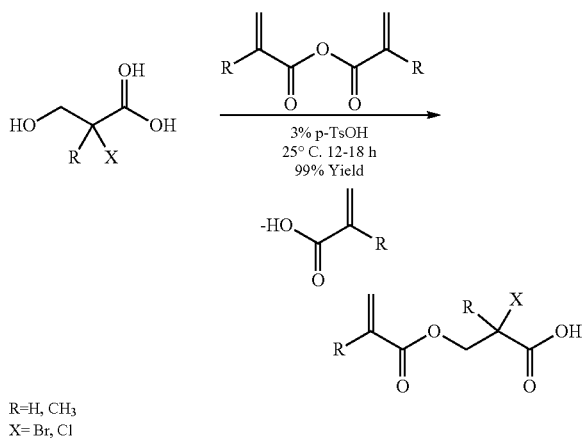

R=H, CH₃
X= Br, Cl

Preparation of Pre-Inimer Acyl Chloride

The pre-inimer may then be reacted with a chlorinating agent to form an acid chloride. For example, 3-methacrylate-2-bromo-2-methylpropionic acid may be reacted with phosphorus pentachloride to yield the corresponding acyl chloride, as shown in Scheme 4.

Scheme 4. Synthesis of 2-bromo-3-chloro-2-methyl-3-oxopropyl methacrylate

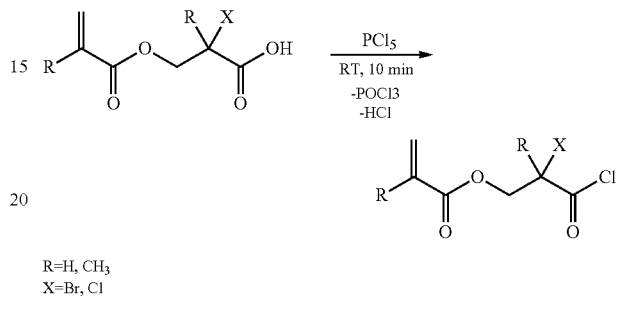

R=H, CH₃
X=Br, Cl

Preparation of Inimers

In one or more embodiments, inimers may be synthesized using the pre-inimer acid or the acyl chloride precursors presented in Scheme 3 and 4. In one or more embodiments, the acid or the acyl chloride efficiently react with a wide variety of molecules containing an alcohol ($R^1OH$) to obtain the corresponding inimers presented in Scheme 5.

Scheme 5A. Synthesis of inimers

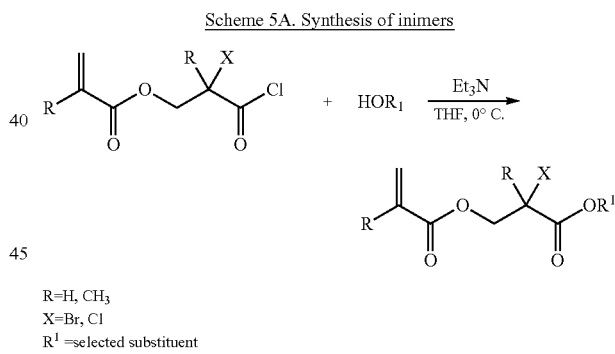

R=H, CH₃
X=Br, Cl
$R^1$ =selected substituent

Advantageously, the inimer containing a carboxylic acid group, i.e. the inimer acid, may be activated to form a pre-inimer acyl chloride to efficiently react with a wide variety of alcohols for reduced reaction times. In this manner, a wide variety of functional groups $R^1$ may be incorporated into inimers via esterification of the pre-inimer with an alcohol. $R^1$ is not particularly limited. In one or more embodiments, $R^1$ may be a moiety selected from aliphatic, non-aliphatic, fluorocarbon, carbohydrate-based (selected from monosaccharaides such as mannose, glucose, galactose, disaccharides such as trehalose, sucrose, maltose, lactose, cellobiose, and other disaccharides, polysaccharides or cyclodextrins in deprotected form or protected form with acetate, isopropylidene, silyl ether protected, ketal protected and chloroacetate protecting groups), protected amines, sulfates, sulfonates, acids, thiols, and ionomer protected species. In one or more embodiments, $R^1$ may be a moiety selected from linear or branched, mesogenic chiral, achiral, hydrocarbon, non-hydrocarbon, selected from fluorocarbon, oligo(oxyethylene) and siloxane substituents, alkyl, aryl, mesogenic group, non-mesogenic groups, aliphatic, non-aliphatic, siloxane, perfluoroalkyl, perfluoroaryl, and other fluorocarbon groups.

In one or more embodiments, the 3-methacrylate-2-bromo-2-methylpropionic acyl chloride may be reacted with butanol in the presence of triethyl amine in tetrahydrofuran at 0° C. to yield butyl 3-methacrylate-2-bromo-2-methylpropionate as presented in Scheme 5Bb. Advantageously, the product can be distilled from the crude reaction mixture. In one or more embodiments, the 3-methacrylate-2-bromo-2-methylpropionic acyl chloride may be reacted with an alcohol such as methanol, 1-dodecanol or α-1,2:3,4-di-O-isopropylidene-6-hydroxy-D-galactopyrannose to yield the corresponding inimers as illustrated in Scheme 5Bb, 5Bc and 5Bd, respectively. Advantageously, the inimers can be purified after liquid-liquid extraction and silica gel chromatography.

Scheme 5B. 2-bromo-3-chloro-2-methyl-3-oxopropyl methacrylate

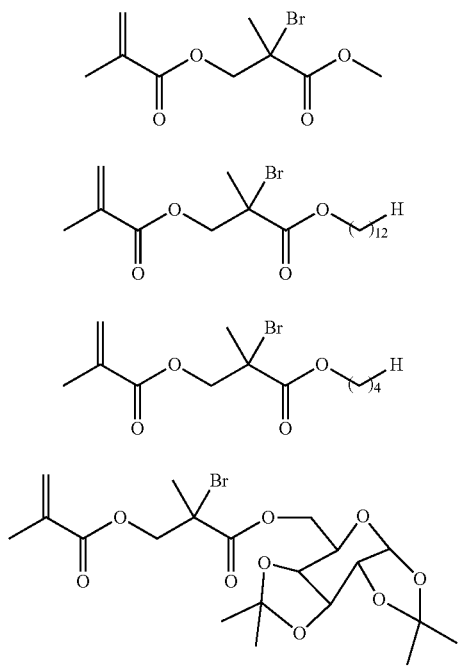

Scheme 5C. Synthesis of inimers using carbodiimide coupling

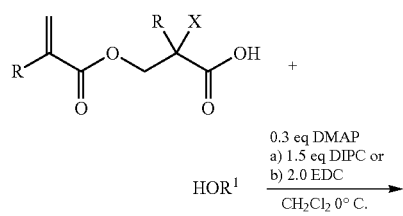

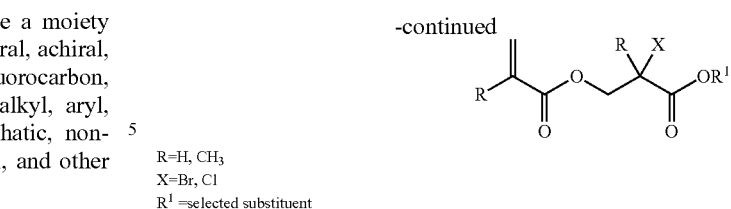

R=H, CH$_3$
X=Br, Cl
$R^1$ =selected substituent

In one or more embodiments, the precursor acyl chloride may be reacted with selectively protected carbohydrates with the protection groups, acetyl- or isopropylidene. Examples of protected carbohydrates include mannose, glucose and galactose.

Other Methods of Preparing Inimers

Other methods to synthesize inimers include the direct esterification of the preinimer acid with alcohols ($R^1OH$) using carbodiimide coupling or the Mitsunobu reaction.

Inimers may be synthesized using carbodiimide coupling. In one or more embodiments, 3-macrylate-2-halo-2-methylpropionic acid or 3-acrylate-2-halopropionic acid may be reacted with ($R^1OH$) alcohols using carbodiimide coupling agents such as 1-ethyl-3-(3-dimethylaminopropyl)carbodiimide hydrochloride (EDC·HCl) or diisopropyl carbodiimide (DIPC) in the presence of 4-dimethylaminopyridine (DMAP) in dichloromethane at room temperature as presented in Scheme 5C. Advantageously, the product can be purified easily because the 1-ethyl-3-(3-dimethylaminopropyl)urea obtained as a byproduct can be removed by liquid-liquid extractions in water and the product can be purified using silica gel chromatography.

Scheme 5D

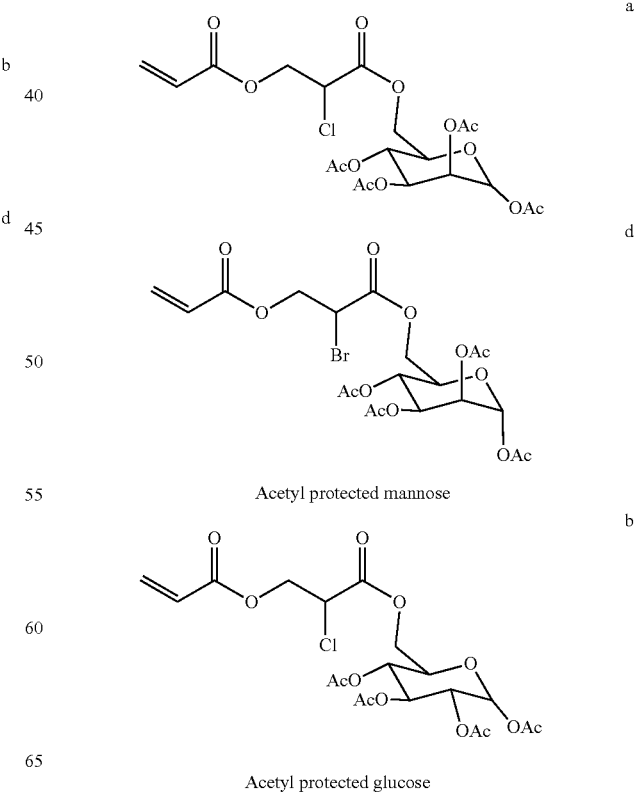

Acetyl protected mannose

Acetyl protected glucose

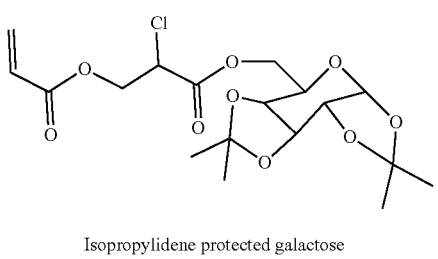

Isopropylidene protected galactose

In one or more embodiments, 3-acrylate-2-halopropionic acid may be reacted with a series of carbohydrate alcohols such as α,β-1,2,3,4-tetra-O-acetyl-6-O-D-manopyranose and α,β-1,2,3,4-tetra-O-acetyl-6-O-D-glucopyranose and α-1,2:3,4-di-O-isopropylidene-6-O-D-galactopyrannose. In one or more embodiments, the chlorinated pre-inimer 3-acrylate-2-chloropropionic may be reacted with the mentioned protected carbohydrates to obtain the inimers presented in Scheme 5Da, 5Db and 5Dc, respectively.

Inimers may be synthesized using the Mitsunobu reaction. In one or more embodiments, 3-macrylate-2-halo-2-methylpropionic acid or 3-acrylate-2-halopropionic acid may be reacted with ($R^1OH$) alcohols using the Mitsunobu reaction with reactants such as triphenylphosphine and diethyl azodicarboxylate (DEAD) in dry THF at 0° C. as presented in Scheme 5E.

Scheme 5E. Synthesis of inimers using carodiimide coupling

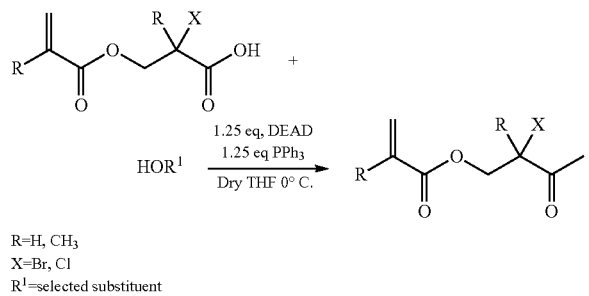

R=H, CH$_3$
X=Br, Cl
R$^1$=selected substituent

In one or more embodiment, 3-acrylate-2-bromopropionic acid may be reacted with α-1,2,3,4-tetra-O-acetyl-6-O-D-manopyranose in the presence of DEAD and triphenylphosphine in dry THF at 0° C. to form α-[1,2,3,4-tetra-O-acetyl-6-O-(2-bromo-3-acrylate)-D-mannopyranose] propionate as presented in FIG. 5Dd. The product can be purified using liquid-liquid extraction and silica gel chromatography.

Polymerization of Inimers

The present invention provides a method to perform homopolymerization of methacrylate and acrylate-based inimers via SCVP and copolymerization of inimers with monomers via SCVCP.

In one or more embodiments, the ester inimers may be homopolymerized to form hyperbranched polymethacrylate and polyacrylate polymers. Hyperbranched polymers were synthesized via SCVP and an ATRP mechanism such as normal atom transfer radical polymerization (ATRP), simultaneous normal and reverse initiated (SN&RI ATRP) and activators regenerated by electron transfer atom transfer radical polymerization ARGET. Scheme 6 illustrates self-condensing vinyl homopolymerization of alkyl (2-halo-2-methyl-3-methacrylate)propionate or alkyl (2-halo-3-acrylate)propionate inimer using (ATRP) and halogen reduction with tin.

Scheme 6

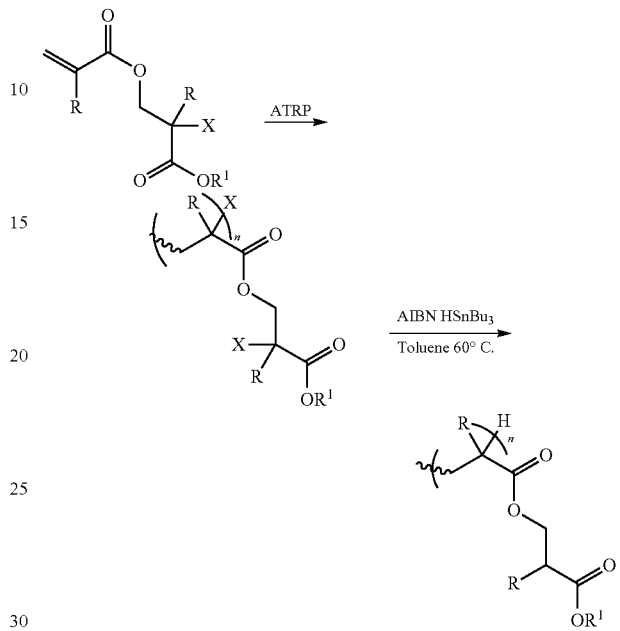

X=Cl, Br
R=H, CH$_3$
R$^1$=selected substituent

The ester inimers may be homopolymerized to form hyperbranched polymethacrylate and polyacrylate polymers. The hyperbranched polymethacrylate polymers prepared according to the method of the present invention are true architectural analogues of linear polymethacrylate polymers. For every repeating unit, there is an ester group attached to every other carbon, with a nonfunctionalized alkyl ester attached as a substituent. Scheme 7 illustrates the self-condensing vinyl homopolymerization of alkyl (2-halo-2-methyl-3-methacrylate)propionate and alkoxy (2-halo-3-acrylate)propionate inimer using (ATRP) compared to linear analogs.

Scheme 7

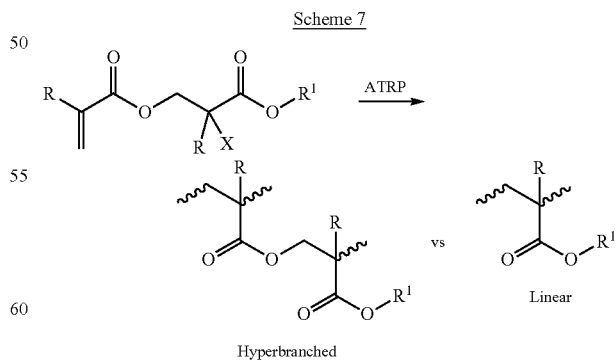

R=H, CH$_3$
X=Br, Cl

Scheme 8 illustrates a) Homopolymerization of butyl (2-Br-2-methyl-3-methacrylate)propionate via normal ATRP b) Homopolymerization of α-[1,2:3,4-di-O-isopropylidene-6-O-(2-bromo-3-acrylate)-D-galactopyrannose propionate] using ARGET and SN&RI and deprotection.

In one or more embodiments, the homopolymerization of butyl 2-Br-2-methyl-3-methacrylate)propionate may be performed using normal ATRP in toluene with the catalyst synthesized using CuBr and N,N,N',N'',N''-pentamethyldiethylenetriamine (PMDETA) in toluene at temperatures from 50-110° C. as presented in Scheme 8a. Depending on the reaction time, the molecular weight of the polymer would increase until crosslinking and gel formation. In one or more embodiments, similar polymerization conditions including various organic solvents such as dioxane, THF, isopropyl alcohol, methanol, etc. or various amine-based ligands such as tris[2-(dimethylamino)ethyl]amine (Me6TREN), 1,4,8,11-Tetramethyl-1,4,8,11-tetraazacyclotetradecane (tetramethyl cyclam), bipyridine, 4,4-di-n-heptyl-2,2-bipyridine and other polyamines, or phosphine-based ligands such as triphenylphosphine, tricyclohexylphosphine and polyphosphines to chelate CuX and $FeX_2$ catalyst species.

Scheme 8 a

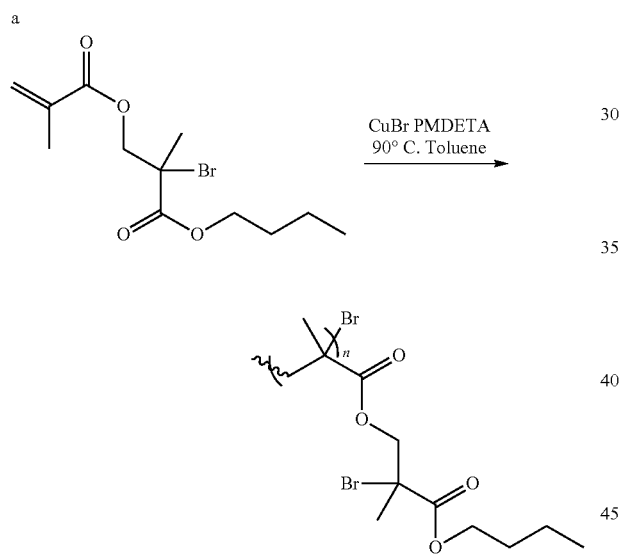

b

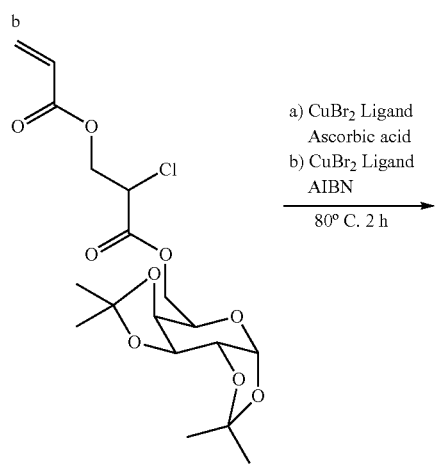

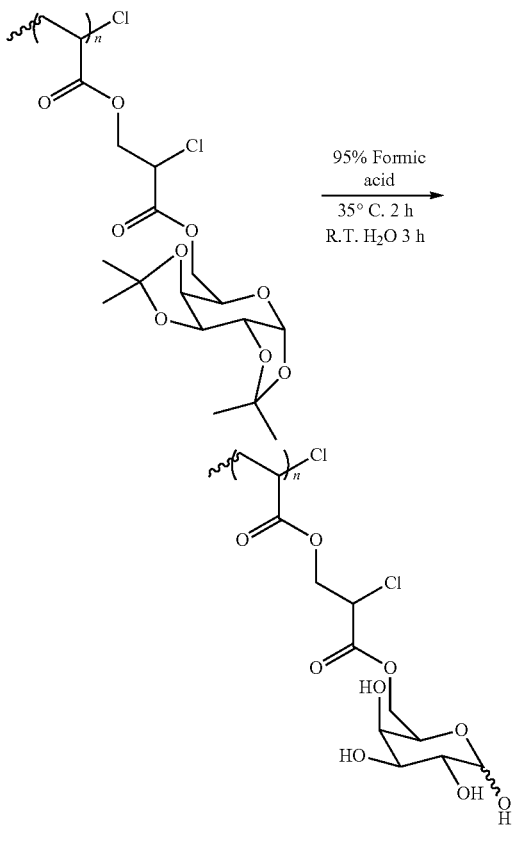

In one or more embodiments, the homopolymerization of α-[1,2:3,4-di-O-isopropylidene-6-O-(2-chloro-3-acrylate)-D-galactopyrannose propionate] may be accomplished using ARGET as presented in Scheme 8b. The polymerization may be performed in the presence of ascorbic acid, $CuCl_2$ complexed with an amine-based ligand in toluene at temperatures from 50° C. to 110° C. The polymer molecular weight increases during 0-15 h and gels may be formed depending on the reaction time and the ratio of reducing agent to catalyst.

In one or more embodiments, the hyperbranched polymer containing α-[1,2:3,4-di-O-isopropylidene-D-galactopyrannose] may be deprotected using formic acid for 2 h at 35° C. for 2 h and then poured in water at room temperature for 3 h. The polymers become gums that can be lyophilized and stored at low temperatures such as −20° C. to prevent degradation.

Scheme 9 illustrates copolymerization of α-[1,2:3,4-di-O-isopropylidene-6-O-(2-chloro-3-acrylate)-D-galactopyrannose propionate] with α-[1,2:3,4-di-O-isopropylidene-6-O-(acrylate)-D-galactopyrannose propionate] using ARGET ATRP. In one or more embodiments, the homopolymerization of α-[1,2:3,4-di-O-isopropylidene-6-O-(2-bromo-3-acrylate)-D-galactopyrannose propionate] using SN&RI ATRP, may be performed in the presence of azobisisobutyronitrile (AIBN), $CuBr_2$ complexed with an amine-based ligand in toluene at temperatures from 50° C.-110° C. Gels were formed between 1-4 h. Gels are obtained in one or more embodiments when the reaction is performed in methanol and in bulk.

Scheme 9

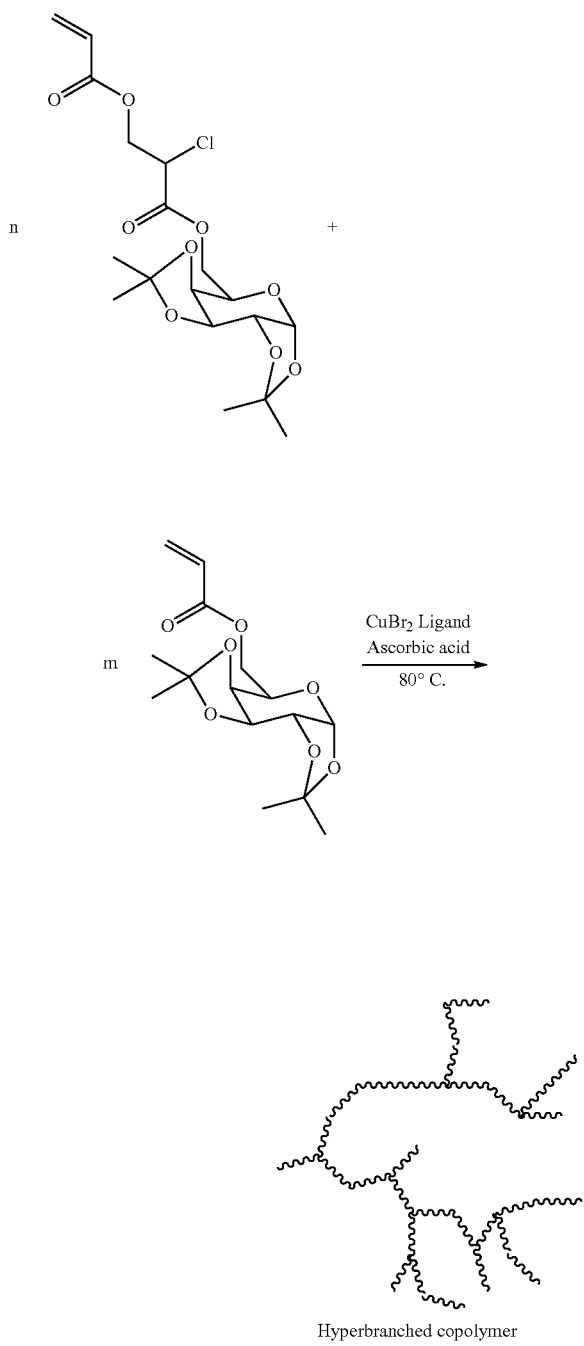

Hyperbranched copolymer

Scheme 11

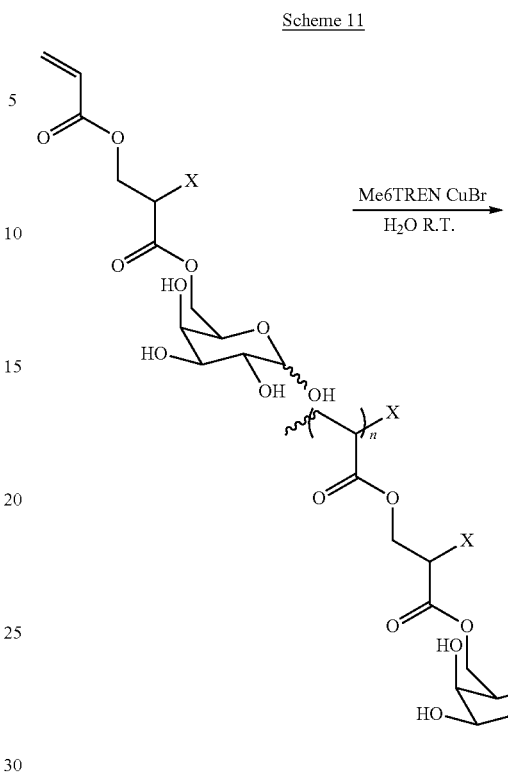

In one or more embodiments, the copolymerization of α-[1,2:3,4-di-O-isopropylidene-6-O-(2-chloro-3-acrylate)-D-galactopyrannose propionate] with the monomer α-[1,2:3,4-di-O-isopropylidene-6-O-(acrylate)-D-galactopyrannose] may be accomplished at various ratios from 1:1 [inimer]:[monomer] to 1:7 [inimer]:[monomer]. The copolymerization may be performed under the same conditions described for SCVP. The copolymer obtained would have lower degree of branching if the molar ratio between monomer and inimer is larger than 1:1, respectively. The copolymers can form a gel at high conversions.

Scheme 11 illustrates the preparation of Hyperbranched polymers based on in aqueous media using for deprotected carbohydrates in aqueous media using SARA ATRP. In one or more embodiments, the SCVP using inimers containing fully deprotected carbohydrates or moieties soluble in aqueous media may be polymerized using supplemental activator and reducing agent atom transfer radical polymerization (SARA ATRP). In one or more embodiments, the mentioned inimers and monomers containing fully deprotected carbohydrates or moieties soluble in aqueous media may be polymerized using SARA ATRP. In one or more embodiments, polymerizations of α-[1,2:3,4-tetra-O-hydroxy-6-O-(2-halo-3-acrylate)-D-galactopyrannose propionate] may be performed at room temperature using CuBr and Me6TREN after purging the solution with nitrogen for 30 min as presented in Scheme 11. After polymerization, hyperbranched glycopolymers may be purified by dialysis, lyophilized and stored at −22° C.

Applications

The hyperbranched polymethacrylates and polyacrylates of the present invention may have have applications as ingredients in coating formulations. The polymers can induce viscosity reduction and introduce large functionality to polymer mixtures, since the inimers could be functionalized with the desired functional group. Functional groups could be added to the hyperbranched polymers for other application, like metal chelation, etc.

Hyperbranched polymers obtained using SCVP and SCVCP of inimers and monomers functionalized with carbohydrates prepared according to the method of the present invention offer special biological properties compared to linear glycopolymers. Hyperbranched polymers have higher adsorption of lectins like $RCA_{120}$ compared to linear polymers. The material could be potentially used in protein capture or protein preservation applications. Additionally, protected proteins with carbohydrates could potentially preserve proteins from temperature excursions.

The hyperbranched polymers have potential for biodegradability since the components of hyperbranched polymers were obtained from aminoacids like serine or methyl serine. The inimer functional groups are connected only through ester groups.

Biodegradable glycopolymers can be used in patches or gels for external applications in the health market. Tissues or other biological relevant molecules might be preserved with the use of this molecules. Hyperbranched glycopolymers can be used in formulations or devices for protein preservation, external skin or would healing. The hyperbranched polymers of the present invention have application for medical devices, biomaterials, polymers and pharmaceuticals.

In order to demonstrate the practice of the present invention, the following examples have been prepared and tested. The examples should not, however, be viewed as limiting the scope of the invention. The claims will serve to define the invention.

EXAMPLES

Synthesis of Methyl Serine

Methyl serine was synthesized using the procedure published by Otani, T. T.; Winitz, N. "Studies on Hydroxyamino Acids. I. Synthesis of Some αAlkylated Serines", Archives of Biochemistry And Biophysics 1960, 90, 254-259, which resulted in 41-65% yield as in the following example. Sodium carbonate (23.319 g, 0.22 mol) was dissolved in DI water (1050 mL). The solution was heated to boil using a heating mantle. D,L-Alanine (10.008 g, 0.11 mol) was dissolved in DI water (50 ml), combined with 1M cupric sulfate (11.2 mL, 0.0112 mol) and then added to the boiling sodium carbonate solution. 37% Aqueous formaldehyde (33 mL, 0.42 mol) was added and the blue solution was stirred at reflux with a water condenser for 40 min. The red precipitate was filtered off using a fritted glass funnel, and the filtrate was acidified with 90 mL glacial acetic acid. An aliquot was taken at this time for NMR analysis, which suggests a full conversion. The solution was separated into two fractions. One fraction was poured onto 242.54 g AR®50WX12 resin (H+ form) and stirred for 12 h. The mixture was washed with DI water (1000 mL) and then transferred to column. The resin was washed with DI water (1000 mL) in twice the volume of the resin bed amount. 0.1 M aqueous ammonium solution (1000 mL) was used to elute the product. The ninhydrin-positive fractions were collected.

After being concentrated to about 50 mL by heating, the solution was precipitated in 200 mL cold ethanol and stored overnight in a freezer at −20° C. The other fraction was also worked up by the procedure above. The white power (7.944 g, yield 59%) was collected on a glass frit in total and was dried in a vacuum oven at room temperature overnight. 1H NMR (300 MHz, Deuterium Oxide) δ=1.40 (s, CH3), 3.63 (d, CHHOH, 2J=12.0 Hz), 3.88 (d,CHHOH, 2J=12.0 Hz). 13C NMR (75 MHz, Deuterium Oxide) δ=18.07 (CH3), 62.03 (CH$_2$OH), 64.37 (CNH2), 174.61 (COOH).

Synthesis of 2-bromo-3-hydroxy-2-methyl-propanic Acid

Sodium nitrite (12.425 g, 0.18 mol) was added in portions over 4 h to a solution of methyl serine (10.729 g, 0.090 mol), HBr (26 mL, 48% aqueous solution, 0.21 mol) and KBr (35.760 g, 0.30 mol) in H$_2$O (80 mL) at approximately −10° C. After stirring at R.T. for 12 h, the light-yellowish solution was saturated with NaCl and extracted with EtOAc (50 mL×5=250 mL). The combined organic extracts were washed with sat. aq. NaCl (50 mL×2=100 mL) and dried over MgSO$_4$. After filtration and removing the solvent by trap-to-trap distillation, the residue was recrystallized from CH2Cl2 to obtain 3.584 g (yield 22%) of 2-bromo-3-hydroxy-2-methylpropionic acid as a white hygroscopic solid. 1H NMR (300 MHz, Deuterium Oxide) δ=1.87 (s, CH3), 3.90 (d, CHHOH, 2J=12.0 Hz), 3.98 (d, CHHOH, 2J=12.0 Hz). 13C NMR (75 MHz, Deuterium Oxide) δ=25.05 (CH3), 61.60 (CBr), 68.72 (CH2), 174.76 (COOH). Anal. Calcd: C, 26.37, H, 3.27. Found: C, 26.18, H, 3.53.

Synthesis of 2-bromo-3-chloro-2-methyl-3-oxopropyl methacrylate

2-Bromo-3-chloro-2-methyl-3-oxopropyl methacrylate was synthesized in 64-80% yield as in the following example. 2-Bromo-3-methacrylic-2-methylpropionic acid (0.871 g, 3.47 mmol) and phosphorus pentachloride (0.866 g, 4.16 mmol) were mixed and stirred for 10 min at room temperature. Phosphorus oxychloride was removed by distillation at 40° C. under 1 mm Hg vacuum. 2-Bromo-3-chloro-2-methyl-3-oxopropylmethacrylate 0.676 g (yield 80%) was distilled and collected at 75° C. at 1 mm Hg vacuum as a colorless liquid. 1H NMR (300 MHz, CDCl3): δ=1.95 (s, CH3CBr), 2.04 (s,CH3C=), 4.53 (d, CHHO2C, 2J=11.4 Hz), 4.67 (d, CHHO2C, 2J=11.4 Hz), 5.65 (s,CHHb=trans to CO2), 6.12 (s, CHaH=cis to CO2). 13C NMR (75 MHz, CDCl3): δ=22 18.27 (CH3C=), 25.96 (CH3CBr), 62.22 (CBr), 69.19 (CH$_2$O2C), 127.18 (methacrylate CH2), 135.32 (C=CH2), 165.83 (methacrylate C=O), 171.61 (C=O).

Synthesis of 2-bromo-3-methoxy-2-methyl-3-oxoproyl methacrylate

2-Bromo-3-methoxy-2-methyl-3-oxoproyl methacrylate was synthesized as in the following example in 96% yield. A solution of 2-bromo-3-chloro-2-methyl-3-oxopropyl methacrylate (0.644 g, 2.390 mmol) in dry THF (4 mL) was added to a solution of methanol (106 μL, 2.629 mmol) and triethylamine (398 μL, 2.87 mmol) in dry THF (11 mL) at 0° C. The mixture was stirred at room temperature for 12 h. The white precipitate was filtered off using a fritted glass filter and the solvent in the filtrate was removed by trap-to-trap distillation. The residue was passed through a plug of basic activated alumina with chloroform. The solvent in the eluant was removed to yield 0.608 g (yield 96%) of 2-bromo-3-methoxy-2-methyl-3-oxoproyl methacrylate as a colorless liquid. 1H NMR (300 MHz, CDCl3) δ=1.93 (s, CH3C=), 1.93 (s, CH3CBr), 3.80 (s, CH3OOC), 4.48 (d, CHHO2C, 2J=11.8 Hz), 4.60 (d, CHHO2C, 2J=11.8 Hz), 5.59 (s, CHHb=trans to CO2), 6.10 (s, CHaH=cis to CO2). 13C NMR (CDCl3): δ=18.29 (CH3C=), 25.65 (CH3CBr), 53.48 (CH3O), 55.27 (CH3CBr), 69.32 (CH2), 126.56 (methacrylate CH2), 135.70 (C=CH2), 166.23 (methacrylate C=O), 170.06 (C=O).

Synthesis of 2-bromo-butoxy-2-methyl-3-oxopropyl methacrylate

2-Bromo-butoxy-2-methyl-3-oxopropyl methacrylate was synthesized in 61% yield as the following example.

2-Bromo-3-methacrylic-2-methyl propionic acid (0.633 g, 2.98 mmol) and phosphorus pentachloride (0.618 g, 2.97 mmol) were mixed and stirred for 12 h at room temperature. Phosphorus oxychloride was removed by distillation at 40° C. under 5 mm Hg vacuum. The black residue was dissolved in 10 mL THF and added slowly to a solution of n-butanol (0.220 g, 2.967 mmol) and dry triethylamine (536 µL, 3.86 mmol) in dry THF (6 mL) at 0° C. The white precipitate was filtered after 2.5 h. The reaction mixture was poured into ice water (50 mL) and stirred for 3 h to partially evaporate THF. Since no more precipitate formed, THF was removed by rotayevaporation and CH2Cl2 (50 mL) was added. After separating the two layers, the organic phase was washed twice with 0.1 M aqueous NaHCO3 (25 mL each), once with sat. aq. NaCl (25 mL), and dried over MgSO4. After filtration and removing the solvent by rotary evaporation, 2-bromo-butoxy-2-methyl-3-oxopropyl methacrylate (0.487 g, 61%) was obtained as a colorless oil. 1H NMR (300 MHz, CDCl3): δ=0.92 (t, CH3CH2, 3J=7.3 Hz), 1.40 (sext, CH3CH2CH2, 3J=7.3 Hz), 1.66 (quin, CH3CH2CH2, 3J=7.3 Hz and 6.5 Hz), 1.93 (s, methacrylate CH3), 1.93 (s, CH3CBr), 4.20 (t, CH3CH2CH2CH2, 3J=6.5 Hz),), 4.45 (d, CHHO2C, 2J=11.3 Hz), 4.64 (d, CHHO2C, 2J=11.3 Hz), 5.60 (s, CHHb=trans to CO2), 6.09 (s, CHaH=cis to CO2) 13C NMR (75 MHz, CDCl3): δ=13.75 (CH3(CH2)3), 18.32 (CH3C=), 19.16 (CH3CH2(CH2)2) 25.65 (CH3CBr), 30.56 (H(CH2)2CH2CH2), 55.59 (CH3CBr), 66.39 (H(CH2)3CH2), 69.39 (CH2CBr) 126.54 (methacrylate CH2), 135.76 (C=CH2), 166.28 (methacrylate C=O), 169.60 (C=O).

Synthesis of 2-bromo-3-(dodecyloxy)-2-methyl-3-oxopropyl methacrylate

2-Bromo-3-(dodecyloxy)-2-methyl-3-oxopropyl methacrylate was synthesized in 74-84% yield as in the following example. A solution of 2-bromo-3-chloro-2-methyl-3-oxopropyl methacrylate (0.834 g, 3.10 mmol) in dry THF (2 mL) was added to a solution of 1-dodecanol (0.634 g, 3.40 mmol) and dry triethylamine (376 µL, 3.71 mmol) in dry THF (15 mL) at 0° C. The mixture was stirred at room temperature for 12 h. The white precipitate was filtered off using a fritted glass funnel (0.422 g, 3.06 mmol) and the solvent in the filtrate was removed by trap-to-trap distillation. The product (Rf=1) was purified by silica gel column chromatography using solution of CHCl3/Hexanes (7/1, v/v) as the eluent to yield 1.096 g (yield 84%) of 2-bromo-3-methoxy-2-methyl-3-oxoproyl methacrylate as a colorless liquid. 1H NMR (300 MHz, CDCl3): δ=0.88 (t, CH3(CH2) 9, 3J=6.9 Hz), 1.2-1.5 (m, (CH2)9), 1.66 (quin, COOCH2CH2, 3J=8.3 and 6.4 Hz), 1.95 (s, methacrylate CH3), 1.95 (s, CH3CBr), 4.19 (t, COOCH2, 3J=6.6 Hz), 4.50 (d, CHHO2C, 2J=11.2 Hz), 4.64 (d, CHHO2C, 2J=11.2 Hz), 5.60 (s, CHHb=trans to CO2), 6.11 (s, CHaH=cis to CO2). 13C NMR (75 MHz, CDCl3): δ=14.25 (CH3(CH2) 11), 18.32 (CH3CH2(CH2)10), 22.83 (methacrylate CH3), 25.65 (H(CH2)2CH2(CH2)9), 25.91 (H(CH2)3CH2(CH2) 8), 28.53 (CH3CBr), 29.31 (H(CH2)4CH2(CH2)7), 29.49 (H(CH2)5CH2(CH2)6), 29.62 (H(CH2)6CH2(CH2)5), 29.70 (H(CH2)7CH2(CH2)4), 29.77 (H(CH2)8CH2(CH2) 3), 29.78 (H(CH2)9CH2(CH2)2), 32.06 (H(CH2) 10CH2CH2), 55.59 (CBr), 66.69 (H(CH2)11CH2), 69.39 (CH2CBr), 126.53 (C=CH2), 135.76 (C=CH2), 166.25 (methacrylate C=O), 169.58 (C=O).

Synthesis of 2-bromo-3-hydroxy-propionic Acid

Synthesis was conducted using the procedure reported in Pugh, C.; Raveendra, B.; Singh, A.; Samuel, R.; Garcia, G. SynLett 2010, 13, 1947-1950, with 63% Yield m.p.=38-39° C. 1H NMR CDCl3/DMSO-d6. $^1$H NMR (500 MHz, CDCl3) δ3.89 (dd, CHHOH, 3J=12.0 Hz, 2J=5.4 Hz), 3.99 (dd, CHHOH, 3J=12.2 Hz, 2J=7.2 Hz), 4.30 (dd, CHBr, 3J=5.8, 3J=7.3 Hz), 7.19 (br, s, CO2H and OH). 13C NMR (125 MHz, CDCl3) δ 45.6 (CHBr), 64.0 (CH$_2$OH), 171.0 (C=O).

Synthesis of 2-chloro-3-hydroxy-propionic Acid

Synthesis was conducted according to the procedure reported in Pugh, C.; Singh, A.; Samuel, R.; Bernal Ramos, K. M. Macromolecules 2010, 43, 5222-5232. 58% Yield mp=28-29° C. 1H NMR CDCl3/DMSO-d6. 1H NMR (500 MHz, CDCl3) δ 3.961 (dd, CHHOH, 3J=11.9 Hz, 2J=5.7 Hz), 4.01 (dd, CHHOH, 3J=12.2 Hz, 2J=5.7 Hz), 4.40 (dd, CHCl, 3J=3J=5.7 Hz), 7.12 (br, s, CO2H and OH). 13C NMR (125 MHz, CDCl3) δ 57.8 (CHCl), 64.3 (CH$_2$OH), 170.4 (C=O).

Synthesis of 3-acrylate-2-bromo propionic Acid

Acrylic anhydride (16.563 g, 91.6 mmol) was added dropwise over 60 s to a mixture of 2-bromo-3-hydroxy propionic acid (16.024 g, 94.8 mmol), p-toluenesulfonic acid (0.888 g, 4.62 mmol) and a catalytic amount of pyrogallol (kernel) to prevent oligomerization. The reaction mixture was stirred at 25° C. and the round bottom flask was covered with aluminum foil until reaction achieved full conversion in 12 h. Then, a trap-to-trap distillation under vacuum at 1 mm Hg was performed, to remove the excess of acrylic anhydride at room temperature. Subsequently, an azeotropic distillation was performed using 10 additions of H$_2$O (20 mL) each time, to remove the acrylic acid produced. To the oil obtained, CH2Cl2 (200 mL) was added and the solution was set in the freezer for 6 h. A white precipitate (p-toluene sulfonic acid) was removed by decanting the supernatant liquid, then the yellow solution was reduced using the rotatory evaporator (crude 21.89 g) and passed through a plug of silica using CH2Cl2/ethyl acetate 50% v. The product was set under vacuum to dry. Yellow oil obtained (21.10 g, 99.8% yield).

$^1$H NMR (500 MHz, CDCl3) δ 4.8-4.53 (m, 2H, HHOC=O, HBrC=OO), 4.66-4.55 (m, 1H, HHOC=O), 5.92 (dd, CHH=CH, 3J=10.40 Hz, 2J=1.35 Hz), 6.14 (dd, CHH=CH, 3J=17.27 Hz, 3J=10.40 Hz), 6.48 (dd, CHH=CH, 2J=1.35 Hz, 3J=17.27 Hz). 13C NMR (125 MHz, CDCl3) δ 40.01 (—BrCH—), 64.07 (—HHC—), 127.33 (=CH), 132.31 (CHH=), 165.26 (—C=OO—), 171.26 (—C=OOH).

In one or more embodiments, where the inhibitor does not prevent oligomerization during the distillation of the acrylic acid, then a gum would be obtained. To remove the oligomers, the gum was dissolved in acetone (3 mL), and added it dropwise to CH$_2$Cl$_2$ (50 mL) at 35° C., to precipitate the oligomers. The liquid was decanted to separate the precipitated gum and the process was repeated 3×. The mother liquor contains unreacted pre-inimer, and the solvent was reduced in the rotatory evaporator.

Synthesis of 3-acrylate-2-chloro propionic Acid

In analogous procedure to obtain 3-acrylate-2-bromo propionic acid, the chloro analog was synthesized using 2-chloro-3-hydroxy propionic acid (99.8% yield). $^1$H NMR (500 MHz, CDCl$_3$) δ 4.64-4.53 (m, 3H, HHOC=O, HHOC=O, HBrC=OO), 4.69 (br, 1H, COOH), 5.92 (dd, CHH=CH, $^3J$=10.43 Hz, $^2J$=1.30 Hz), 6.15 (dd, CHH=CH, $^3J$=17.30 Hz, $^3J$=10.43 Hz), 6.47 (dd, CHH=CH, $^2J$=1.30 Hz, $^3J$=17.30 Hz). $^{13}$C NMR (125 MHz, CDCl$_3$) δ 53.42 (—ClCH—), 64.33 (—HHC—), 127.30 (=CH), 132.37 (CHH=), 165.36 (—C=OO—), 171.72 (—C=OOH).

Inimer Synthesis Using Carbodiimide Coupling (EDC). β-[1,2,3,4-tetra-O-acetyl-6-O-(2-bromo-3-acrylate)-D-mannopyranose] propionate A suspension of EDC·HCl (0.414 g, 2.159 mmol) in CH$_2$Cl$_2$ (7 mL) was added dropwise through an addition funnel over 5 min at room temperature to a solution of β-1,2,3,4-tetra-O-acetyl-6-O-D-mannopyranose (0.305 g, 0.875 mmol), 3-acroyloyl-2-bromo propionate (0.252 g, 1.129 mmol) and DMAP (0.031 g, 0.253 mmol) in dry CH$_2$Cl$_2$ (1 mL). The reaction became yellow-orange, and was quenched after 4 h by adding H$_2$O (10 mL), then extracted with H$_2$O (10 mL) 5x. After that, the organic phase was dried over MgSO$_4$, filtered and reduced in the rotatory evaporator. The crude product obtained (0.433 g, 89.6%) was purified using flash chromatography in a solvent gradient from CH$_2$Cl$_2$:acetone 10:0.5 v to 10:1 v to obtain a transparent oil (0.23 g, crude 56.5%). This reaction should be worked up before 5 h, because β-H elimination could otherwise take place. For a anomer mannose, Yield: 54% $^1$H NMR (500 MHz, CDCl$_3$) δ 2.02 (s, 3H, H-16). 2.07 (s, 3H, H-16), 2.17 (s, 3H, H-16), 2.18 (s, 3H, H-16), 4.11-4.04 (m(ddd), 1H, H-5), 4.28 (dd, 1H, $^2J_{6a,6b}$=12.37 Hz, $^3J_{6a,5}$=2.37 Hz, H-6a), 4.36 (ddd, 1H, $^2J_{6b,6a}$=12.37 Hz, $^3J_{6b,5}$=4.61 Hz, H-6b), 4.66-4.56 (m, 1H, H-8), 4.66-4.48 (m, 2H, H-9, H-10), 5.29-5.25 (m (dd), 1H, H-3), 5.38-5.33 (m (dd, t), 2H, H-2, H-4), 5.90 (dd, 1H, $^3J_{13,12}$=10.44 Hz, $^2J_{13,14}$=1.16 Hz, H-13), 6.08 (d, 1H, $^3J_{1\alpha,2}$=1.84 Hz, H-1), 6.14 (dd, 1H, $^3J_{12,14}$=17.21 Hz, $^3J_{12,13}$=10.44 Hz, H-12), 6.46 (dd, 1H, $^3J_{14,12}$=17.21 Hz, $^2J_{14,13}$=1.16 Hz, H-14). $^{13}$C NMR (125 MHz, CDCl$_3$) δ 20.61 (C-16), 20.62 (C-16), 20.70 (C-16), 20.82 (C-16), 40.57 (C-8), 63.65 (C-6), 64.05 (C-9), 65.53 (C-2), 68.31 (C-3), 68.57 (C-4), 70.42 (C-5), 90.44 (C-1), 127.49 (C-12), 132.00 (C-13), 165.12 (C-10), 167.01 (C-7), 167.96 (C-15), 169.51 (C-15), 169.70 (C-15), 169.33 (C-15).

Synthesis of Inimer Using Carbodiimide Coupling (DIPC) α-[1,2,3,4-tetra-O-acetyl-6-O-(2-chloro-3-acrylate)-D-mannopyranose] propionate A solution of DIPC (0.177 g, 1.41 mmol) in 2 mL of CH$_2$Cl$_2$ was added dropwise over 1 min to a stirred solution of α-1,2,3,4-tetra-O-acetyl-6-O-D-mannopyranose (0.40 g, 1.15 mmol), DMAP (0.035 g, 0.286 mmol) and 3-acryloyl-2-chloro-propionic acid (0.303 g, 1.56 mmol) in 3.6 mL of CH$_2$Cl$_2$ at 0° C. After 2 h, the reaction was poured into hexanes (5 mL) and filtered at 0° C. Urea was precipitated in hexanes/dichloromethane 50% v (10 mL) 3x at −20° C. and removed by filtration. The filtrate was reduced under the rotatory evaporator, then a gradient column was performed in a solvent system from CH$_2$Cl$_2$ 100% to CH$_2$Cl$_2$:acetone 10:1 v to obtain a transparent oil (0.5481 g, 94%) with traces of urea.

The analogous procedure for brominated inimer yields 81.8%.

Inimer Synthesis Using Mitsunobu Reaction α-[1,2,3,4-tetra-O-acetyl-6-O-(2-bromo-3-acrylate)-D-mannopyranose] propionate A solution of DEAD (0.187 g, 1.07 mmol) in 3 mL of THF was added to a solution of α-1,2,3,4-tetra-O-acetyl-6-O-D-mannopyranose (0.304 g, 0.87 mmol), and PPh$_3$ (0.271 g, 1.03 mmol) in 3 mL of dry THF at 0° C. Then, a solution of 3-acryloyl-2-bromo-propionic acid (0.239 g, 1.07 mmol) in THF (3 mL) was added dropwise over 3 minutes. The reaction was stirred at room temperature for 24 h, then quenched in H$_2$O (10 mL), and extracted with CH$_2$Cl$_2$ (15 mL) 3x. Subsequently, the organic phase was dried over MgSO$_4$, filtered and reduced the volume using the rotatory evaporator to obtain an oil. Then, a column in a gradient solvent system from hexanes 100% to hexanes:acetone 10:3 v. was performed. The product obtained was a transparent oil (0.386 g, 78.0%).

Synthesis of Hyperbranched Polymers Using SR&NI ATRP (α,β-[1,2,3,4-tetra-O-acetyl-6-O-(2-bromo-3-acrylate)-D-mannopyranose] propionate)

A ($2.13*10^{-1}$ M) stock solution of equimolar concentration of PMDETA and CuBr$_2$ in acetonitrile (1.35 mL, $2.84*10^{-1}$ mmol) was added to the Schlenk flask. Then, the acetonitrile was removed in a trap-to-trap for 20 minutes. After that, a solution of α,β-[1,2,3,4-tetra-O-acetyl-6-O-(2-bromo-3-acrylate)-D-mannopyranose] propionate (1.514 g, 2.84 mmol), 5 drops of amyl acetate and anisole (0.4 mL) was added under positive nitrogen flow. The solution was frozen in liquid nitrogen and degassed by three F-P-T cycles for 5 min-10 min-5 min, respectively. Then, while the solution was frozen in liquid nitrogen, AIBN (0.437 g, 2.88 mmol) was added to the Schlenk flask and degassed by five F-P-T cycles, backfilled the flask with nitrogen and the solution was stirred at 110° C. The polymerization was quenched at 48 h, by setting the Schlenk tube in liquid nitrogen and opened the flask to air. Subsequently, the product was dissolved in THF (20 mL), and passed through basic alumina twice to remove the copper complexes. The solvent was reduced under the rotatory evaporator, then dissolved in THF (0.1 mL) and precipitated in methanol (10 mL) at 0° C. The suspension was centrifuged (4900 r/min for 6 min) and the precipitate was dried under vacuum. Then, the precipitation was repeated. (0.923 g, 61% yield). GPC$_{PS}$ M$_n$=6.00 kDa, Đ=1.52.

Synthesis of Hyperbranched Polymers Using ARGET ATRP α,β-[1,2,3,4-tetra-O-acetyl-6-O-(2-bromo-3-acrylate)-D-mannopyranose] propionate A (17.8 mM) stock solution of PMDETA and CuBr$_2$ in acetonitrile (1.97 mL, 3.51 mmol) of equimolar concentration was added to the Schlenk flask. Then, the acetonitrile was removed by a trap-to-trap distillation for 20 minutes. After that, a solution of α,β-[1,2,3,4-tetra-O-acetyl-6-O-(2-bromo-3-acrylate)-D-mannopyranose] propionate (0.200 g, $3.36*10^{-1}$ mmol), 5 drops of amyl acetate and anisole (0.224 mL) was added to the flask under positive nitrogen flow. The solution was frozen in liquid nitrogen and degassed by five F-P-T cycles for 5 min-10 min-5 min, respectively. Then, over positive nitrogen atmosphere and the flask under liquid nitrogen, Cu(0) (11.1 mg, $1.75*10^{-2}$ mmol) was added, and degassed again by 3 F-P-T cycles. After that, the flask was backfilled with nitrogen, and the solution was stirred at 110° C. The polymerization was quenched at 48 h, by setting the Schlenk tube in liquid nitrogen and opened the flask to air, then dissolved in CHCl$_3$ (2 mL) and extracted with a saturated solution of ammonium chloride (2 mL) 3x, and once with H$_2$O (2 mL). The organic phase was reduced in the rotatory evaporator, and precipitated in solution H$_2$O:MeOH 7:3 v (5 mL) at 0° C., the supernatant liquid was decanted and the gum obtained was dried in the vacuum oven. Yield (169 mg, 84%). GPC$_{PS}$ M$_n$=1.10 kDa, Đ=1.01, GPC$_{LS}$ M$_n$=38.6 kDa, Đ=1.38.

Synthesis of Hyperbranched Copolymers Using ARGET ATRP (α-[1,2:3,4-di-O-isopropylidene-6-O-(2-chloro-3-acrylate)-D-galactopyrannose propionate] and α-[1,2:3,4-di-O-isopropylidene-6-O-(acrylate)-D-galactopyrannose])

A (206 mM) stock solution of an anime-based ligand in methanol (115.0 µL, 2.4*10$^{-2}$ mmol) was added to CuCl$_2$ (3.2 mg, 2.4*10$^{-2}$ mmol) in a Schlenk flask and stirred for 30 min. After that, a solution of α-[1,2:3,4-di-O-isopropylidene-6-O-(2-chloro-3-acrylate)-D-galactopyrannose propionate] (6) (0.500 g, 1.88 mmol), 5 drops of amyl acetate and toluene (1.0 mL) was added to the flask under positive nitrogen flow. The solution was frozen in liquid nitrogen and degassed by 3 F-P-T cycles for 5 min-10 min-5 min, respectively. After that, ascorbic acid was added (6.3 mg, 3.56*10$^{-2}$ mmol) and 2 F-PT cycles were performed. The flask was backfilled with nitrogen, and the solution was stirred at 80° C. The polymerization was quenched at 17 h by setting the Schlenk tube in liquid nitrogen and opened the flask to air, then dissolved in CHCl$_3$ (2 mL) and extracted with a saturated solution of ammonium chloride (2 mL) 3×. The mixture was introduced in a centrifuge for 5 min at 3000 rpm for each extraction and extracted once with H$_2$O (2 mL). The organic phase was reduced in the rotatory evaporator, and precipitated in solution MeOH (4 mL) at 0° C., the supernatant liquid was decanted and the gum obtained was dried in the vacuum oven. Yield (mg, %). GPC$_{PS}$ M$_n$=kDa, Đ=, GPC$_{LS}$ M$_n$=kDa, Đ=.

Deprotection of Hyperbranched Isopropylidene Based Galactose Polymer.

The polymer was deprotected using a modified the procedure reported in Liau, W. T.; Bonduelle, C.; Brochet, M.; Lecommandoux, S.; Kasko, A. M. Biomacromolecules 2015, 16, 284-294.

The polymer (80 mg, 6.0*10$^{-3}$ mmol) was dissolved in formic acid solution (5.0 mL, 1.3*10$^2$ mmol, 95% v) and stirred room temperature for 2 h, then added deionized H$_2$O (5 mL) for 3 h. The solution was cooled to room temperature and poured into a dialysis bag, which was placed into fresh deionized water (500 mL). The water was changed every 6 h for 24 h and then the aqueous phase was removed by lyophilization at 1 mmHg. A slightly yellow orange powder was obtained (50 mg, 82%).

Protein Absorption 3.28. Quartz crystal microbalance studies.

The lectins PNA and Con A were dissolved in deionized Milli-Q water, and the lectin RCA$_{120}$ was used in the original pH buffer from the manufacturer. Deionized water Milli-Q was used to flow above the sensors until a flat baseline was achieved at flow rate of 0.150 mL/min. Lectin aqueous solutions in concentrations for Con A=1.25 µM, PNA=0.091 µM, RCA$_{120}$=2.62 µM were flowed above the sensors until a flat line was achieved, then a solution of D-Galactose (472 µM), linear (M$_n$=39.6 kDa, 3.65 µM) or hyperbranched (M$_n$=61.5 kDa, 2.62 µM) glycopolymer was passed through the flow cell until a flat line was achieved. The change of frequency was recorded and used for calculations.

ATRP of 2-bromo-3-methoxy-2-methyl-3-oxoproyl methacrylate

In a typical procedure, Cu(I)Br (1.43 mg, 0.01 mmol) and PMDETA (1.80 mg, 0.01 mmol) were add to a dry Schlenk tube from 0.052 mmol/ml Cu(I)Br/PMDETA toluene stock solution. 2-bromo-3-methoxy-2-methyl-3-oxoproyl methacrylate (0.129 g, 0.486 mmol) was dissolved in toluene (200 µL) and added under a stream of nitrogen, and the tube was sealed with a glass stopper. After stirring at room temperature for 10 min, the inimer mixture was degassed by five freeze-(30 min) pump-thaw cycles, and the polymerization tube was backfilled with N2. The polymerization mixture was stirred at 90° C. for 14 h, and then the polymerization was quenched by immersing the Schlenk tube into liquid N2. The contents of the polymerization tube were exposed, thawed to the atmosphere, diluted with THF (2 mL) and passed through a plug of activated basic alumina. The eluent was concentrated by rotevaporation and precipitated from THF (1 mL) into methanol/water (7/3 v/v) (5 mL) to yield 0.045 g (34%) of hyperbranched poly(methyl methacrylate) as white flakes. GPCPSt M☐=2.20×103, PDI=1.67.

ATRP of 2-bromo-3-butoxy-2-methyl-3-oxopropyl methacrylate 2-bromo-3-methoxy-2-methyl-3-oxoproyl methacrylate (0.126 g, 0.410 mmol) was added under a stream of nitrogen to a well-stirred suspension of CuBr (12.4 mg, 0.086 mmol), PMDETA (0.0191 g, 0.110 mmol) and toluene (600 µL) in a dry Schlenk tube, and the tube was sealed with a glass stopper. After stirring at room temperature for 10 min, the inimer mixture was degassed by five freeze-(30 min) pump-thaw cycles, and the polymerization tube was backfilled with N2. The polymerization mixture was stirred at 90 for 24 h, and then the polymerization was quenched by immersing the Schlenk tube into liquid N2. The contents of the polymerization tube were exposed, thawed to the atmosphere, diluted with THF (5 mL) and passed through a plug of activated basic alumina. The eluent was concentrated by rotaevaporation and precipitated from THF (1 mL) into methanol/water (7/3 v/v) (5 ml) to yield 0.068 g (54%) of hyperbranched poly(n-butyl methacrylate) as a slightly yellow gum. GPCPSt Mn=2.07×103, PDI=1.56.

ATRP of 2-bromo-3-dodecyloxy-2-methyl-3-oxopropyl methacrylate in Bulk

In a typical procedure, 2-bromo-3-dodecyloxy-2-methyl-3-oxoproyl methacrylate (1.004 g, 2.394 mmol) was added under a stream of nitrogen to CuBr (6.87 mg, 0.048 mmol) and PMDETA (8.46 mg, 0.048 mmol) in a dry Schlenk tube, and the tube was sealed with a glass stopper. After stirring at room temperature for 10 min, the inimers mixture was planned to be degassed by five freeze-(30 min) pump-thaw cycles, but the polymerization happened during the second cycle. THF (6 mL) and toluene (0.5 mL) was used to dissolve the gum. The solution was passed through a basic alumina plug. The elute was concentrated by rotaevaporation, precipitated from THF (4 mL) into methanol (50 mL) and reprecipitated from THF (8.5 mL) into methanol (50 mL) to yield 0.622 g (62%) of hyperbranched poly(dodecyl methacrylate) as an opaque gum. GPCPMMA M☐=21.2×103, PDI=2.29.

ATRP of 2-bromo-3-dodecyloxy-2-methyl-3-oxopropyl methacrylate in Solution

In a typical procedure, 2-bromo-3-dodecyloxy-2-methyl-3-oxoproyl methacrylate (0.405 g, 0.966 mmol) was added under a stream of nitrogen to a well-stirred suspension of CuBr (2.94 mg, 0.0205 mmol), PMDETA (3.54 mg, 0.0204 mmol) and toluene (500 µL) in a dry Schlenk tube, and the tube was sealed with a glass stopper. After stirring at room temperature for 10 min, the inimers mixture was degassed by five freeze-(10 min) pumpthaw cycles, and the polymerization tube was backfilled with N2. The polymerization mixture was stirred at 90° C. for 48 h, and then the polymerization was quenched by immersing the Schlenk tube into liquid N2. The contents of the polymerization tube were thawed, exposed to the atmosphere, diluted with THF (5 mL) and passed through basic alumina plug. The elute was concentrated by rotaevaporation, precipitated from THF (0.5 mL) into methanol (5 mL) and reprecipitated from THF (0.5 mL) into methanol (5 mL) to yield 0.269 g (66%) of hyperbranched poly(dodecyl methacrylate) as an opaque gum. GPCPMMA M□=5.23×103, PDI=1.63.

Various modifications and alterations that do not depart from the scope and spirit of this invention will become apparent to those skilled in the art. This invention is not to be duly limited to the illustrative embodiments set forth herein.

What is claimed is:

1. A method for preparing hyperbranched polyacrylates or polymethacrylates, the method comprising:
   (a) reacting a halohydrin containing a carboxylic acid group with an acrylic anhydride or methacrylic anhydride in the presence of p-toluenesulfonic acid (pTsOH) as an acid catalyst, to form a pre-inimer that contains a carboxylic acid group, wherein the step of reacting a halohydrin containing a carboxylic acid group with an acrylic anhydride or methacrylic anhydride comprises the following reaction:

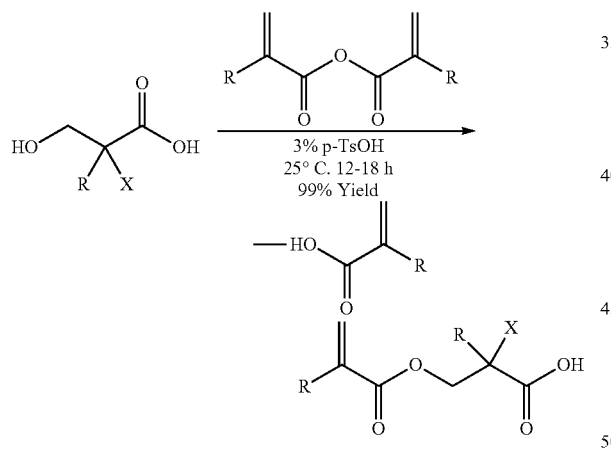

wherein R is methyl and wherein X is bromine or chlorine;
   (b) reacting the pre-inimer with a chlorinating agent to form an acid chloride;
   (c) reacting the acid chloride with an alcohol in the presence of trimethylamine to esterify the acid chloride and form an inimer, wherein the step of reacting the acid chloride with an alcohol comprises the following reaction:

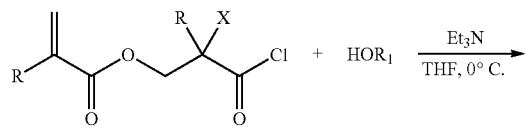

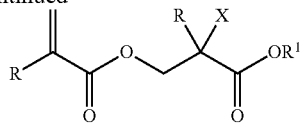

wherein R is methyl, wherein X is bromine or chlorine, and wherein R¹ is selected from aliphatic, non-aliphatic, fluorocarbon, monosaccharides, disaccharides, polysaccharides, cyclodextrins in deprotected form or protected form with acetate, isopropylidene, silyl ether, ketal or chloroacetate protecting groups, protected amines, sulfates, sulfonates, acids, thiols, ionomer species, linear or branched, mesogenic chiral, achiral, hydrocarbon, non-hydrocarbon, fluorocarbon, oligo(oxyethylene), siloxane, mesogenic group, non-mesogenic groups, aliphatic, non-aliphatic, perfluoro alkyl, and perfluoroaryl groups; and
   (d) polymerizing the inimer to form a hyperbranched polyacrylate or polymethacrylate polymer by self-condensing vinyl polymerization, or copolymerizing the inimer with one or more monomers using self-condensing vinyl co-polymerization.

2. The method of claim 1, wherein the halohydrin containing a carboxylic acid group is prepared by a process comprising the following reaction:

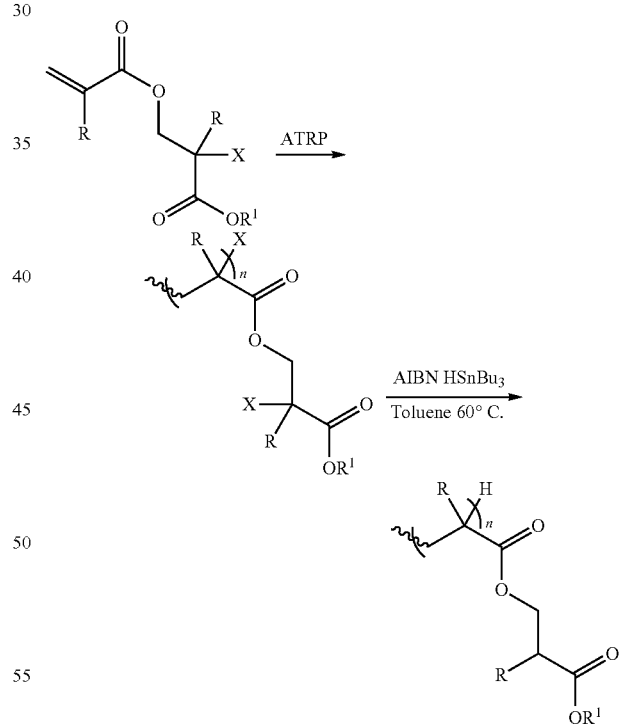

wherein R is methyl and wherein X is bromine or chlorine.

3. A method for preparing hyperbranched polyacrylates or polymethacrylates, the method comprising:
   (a) reacting a halohydrin containing a carboxylic acid group with an acrylic anhydride or methacrylic anhydride in the presence of p-toluenesulfonic acid (p-TsOH), to form a pre-inimer that contains a carboxylic acid group;

(b) reacting the pre-inimer with a chlorinating agent to form an acid chloride;
(c) reacting the acid chloride with an alcohol in the presence of trimethylamine to esterify the acid chloride and form an inimer; and
(d) polymerizing the inimer to form a hyperbranched polyacrylate or polymethacrylate polymer by self-condensing vinyl polymerization, or copolymerizing the inimer with one or more monomers using self-condensing vinyl co-polymerization;
wherein the halohydrin containing a carboxylic acid group is prepared by a process comprising the following reaction:

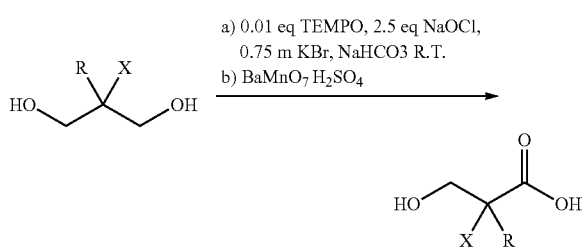

wherein R is hydrogen or methyl and wherein X is bromine or chlorine.

4. A method for preparing hyperbranched polyacrylates or polymethacrylates, the method comprising:
(a) reacting a halohydrin containing a carboxylic acid group with an acrylic anhydride or methacrylic anhydride in the presence of p-toluenesulfonic acid (p-TsOH), to form a pre-inimer that contains a carboxylic acid group;
(b) reacting the pre-inimer with a chlorinating agent to form an acid chloride;
(c) reacting the acid chloride with an alcohol in the presence of trimethylamine to esterify the acid chloride and form an inimer; and
(d) polymerizing the inimer to form a hyperbranched polyacrylate or polymethacrylate polymer by self-condensing vinyl polymerization, or copolymerizing the inimer with one or more monomers using self-condensing vinyl co-polymerization;
wherein the halohydrin containing a carboxylic acid group is prepared by a process comprising the following reaction:

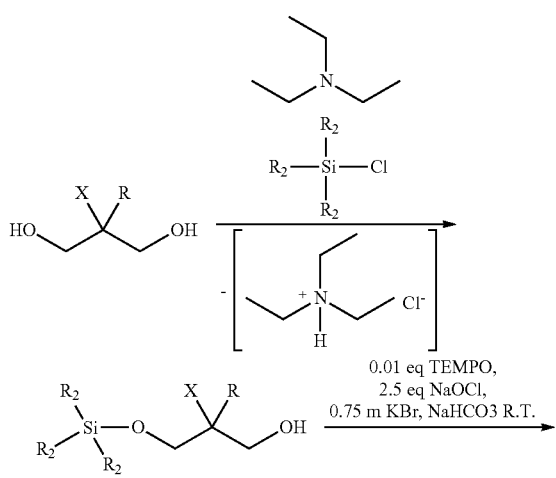

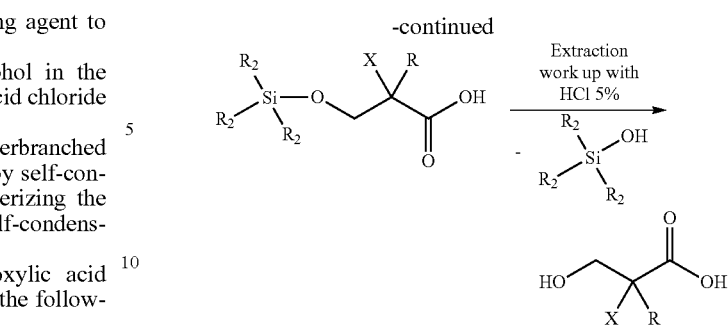

wherein R is hydrogen or methyl, 1e is methyl, ethyl, isopropyl, terbutyl, or diphenyl, and X is bromine or chlorine.

5. A method for preparing hyperbranched polyacrylates or polymethacrylates, the method comprising:
(a) reacting a halohydrin containing a carboxylic acid group with an acrylic anhydride or methacrylic anhydride in the presence of p-toluenesulfonic acid (pTsOH) as an acid catalyst, to form a pre-inimer that contains a carboxylic acid group, wherein the step of reacting a halohydrin containing a carboxylic acid group with an acrylic anhydride or methacrylic anhydride comprises the following reaction:

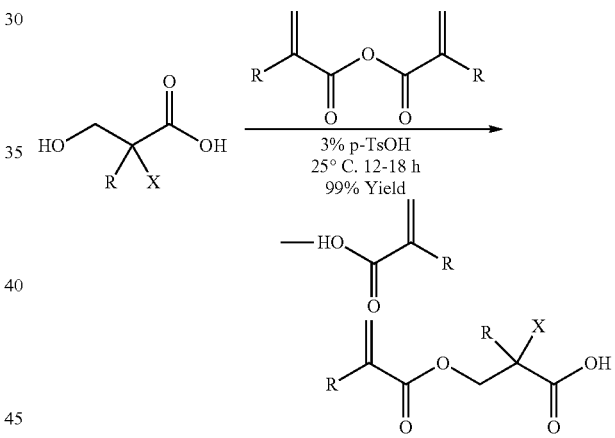

wherein R is methyl and wherein X is bromine or chlorine;
(b) reacting the pre-inimer with an alcohol using carbodiimide coupling or a Mitsunobu reaction to form an ester inimer; and
(c) polymerizing the ester inimer to form a hyperbranched polyacrylate or polymethacrylate polymer by self-condensing vinyl polymerization, or copolymerizing the ester inimer with one or more monomers using self-condensing vinyl co-polymerization.

6. The method of claim 5, wherein the step of reacting the pre-inimer with an alcohol comprises the following reaction:

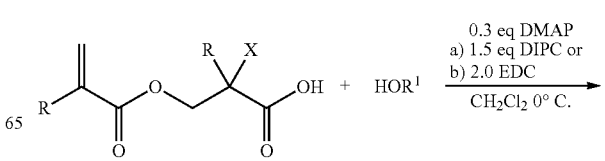

-continued

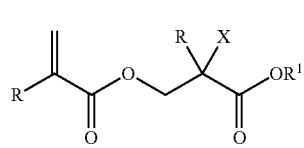

wherein R is methyl, wherein X is bromine or chlorine, and wherein R¹ is selected from aliphatic, non-aliphatic, fluorocarbon, monosaccharides, disaccharides, polysaccharides, cyclodextrins in deprotected form or protected form with acetate, isopropylidene, silyl ether, ketal or chloroacetate protecting groups, protected amines, sulfates, sulfonates, acids, thiols, ionomer species, linear or branched, mesogenic chiral, achiral, hydrocarbon, non-hydrocarbon, fluorocarbon, oligo(oxyethylene), siloxane, mesogenic group, non-mesogenic groups, aliphatic, non-aliphatic, perfluoro alkyl, and perfluoroaryl groups.

7. The method of claim 5, wherein the step of reacting the pre-inimer with an alcohol comprises the following reaction:

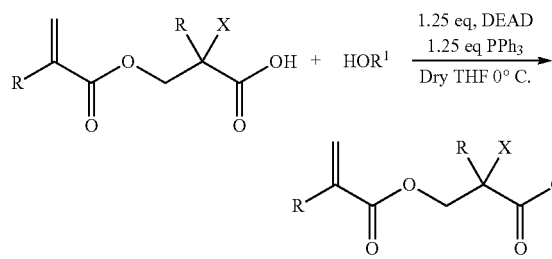

wherein R is methyl, wherein X is bromine or chlorine, and wherein R¹ is selected from aliphatic, non-aliphatic, fluorocarbon, monosaccharides, disaccharides, polysaccharides, cyclodextrins in deprotected form or protected form with acetate, isopropylidene, silyl ether, ketal or chloroacetate protecting groups, protected amines, sulfates, sulfonates, acids, thiols, ionomer species, linear or branched, mesogenic chiral, achiral, hydrocarbon, non-hydrocarbon, fluorocarbon, oligo(oxyethylene), siloxane, mesogenic group, non-mesogenic groups, aliphatic, non-aliphatic, perfluoro alkyl, and perfluoroaryl groups.

8. A method for preparing hyperbranched polyacrylates or polymethacrylates, the method comprising:
(a) reacting a halohydrin containing a carboxylic acid group with an acrylic anhydride or methacrylic anhydride in the presence of p-toluenesulfonic acid (p-TsOH), to form a pre-inimer that contains a carboxylic acid group;
(b) reacting the pre-inimer with an alcohol using carbodiimide coupling or a Mitsunobu reaction to form an ester inimer; and
(c) polymerizing the ester inimer to form a hyperbranched polyacrylate or polymethacrylate polymer by self-condensing vinyl polymerization;

wherein the step of polymerizing the ester inimer comprises either reaction a below or reaction b below:

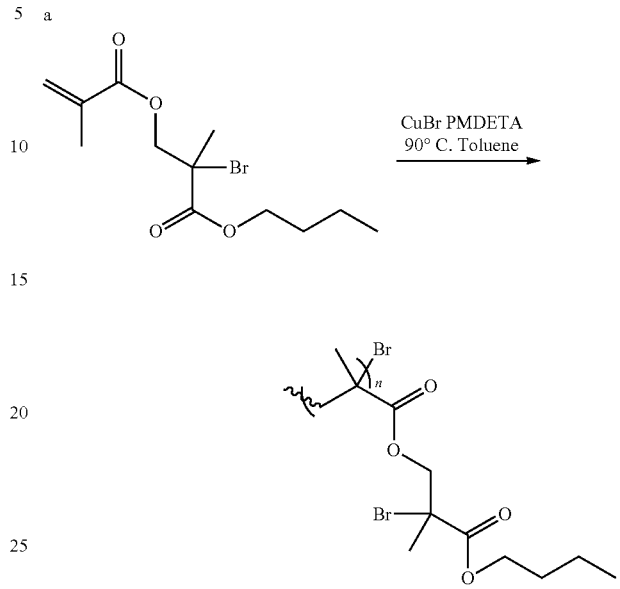

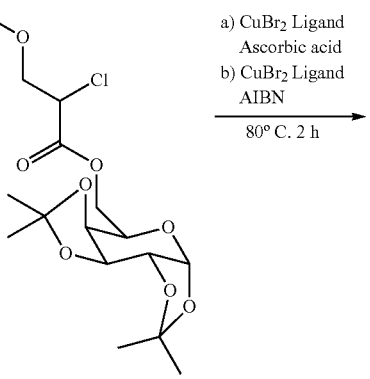

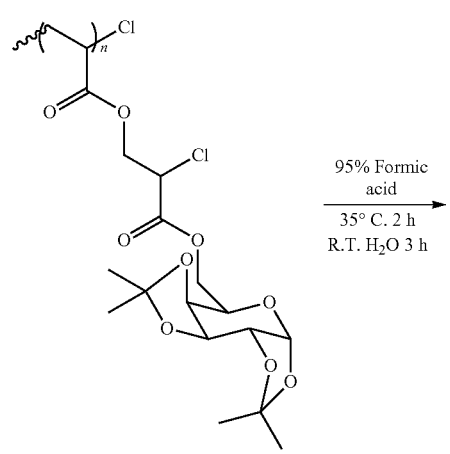

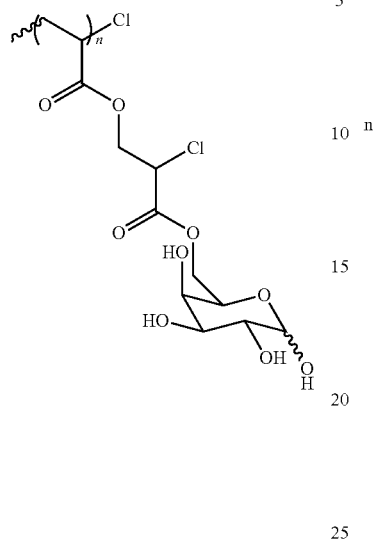

9. A method for preparing hyperbranched polyacrylates or polymethacrylates, the method comprising:

(a) reacting a halohydrin containing a carboxylic acid group with an acrylic anhydride or methacrylic anhydride in the presence of p-toluenesulfonic acid (p-TsOH), to form a pre-inimer that contains a carboxylic acid group;

(b) reacting the pre-inimer with an alcohol using carbodiimide coupling or a Mitsunobu reaction to form an ester inimer; and (c) copolymerizing the ester inimer with one or more monomers using self-condensing vinyl co-polymerization;

wherein the step of copolymerizing the ester inimer comprises the following reaction:

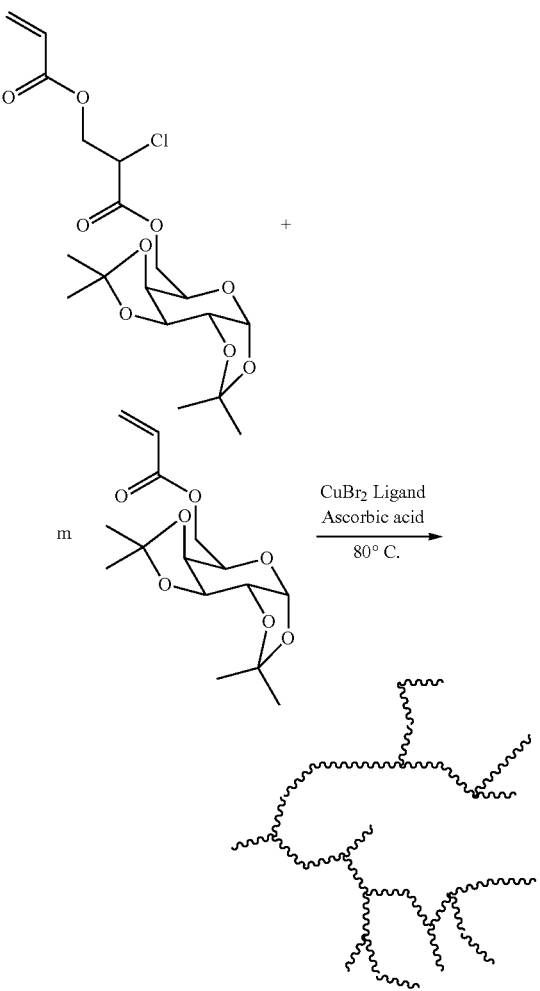

* * * * *